US008034002B2

(12) United States Patent
Coifman

(10) Patent No.: US 8,034,002 B2
(45) Date of Patent: Oct. 11, 2011

(54) APPARATUS AND METHOD FOR INTELLIGENT ELECTRONIC PEAK FLOW METERS

(76) Inventor: Robert E. Coifman, Millville, NJ (US)

(*) Notice: Subject to any disclaimer, the term of this patent is extended or adjusted under 35 U.S.C. 154(b) by 0 days.

(21) Appl. No.: 11/378,058

(22) Filed: Mar. 17, 2006

(65) Prior Publication Data
US 2006/0253045 A1 Nov. 9, 2006

Related U.S. Application Data

(60) Provisional application No. 60/662,605, filed on Mar. 17, 2005.

(51) Int. Cl.
A61B 5/08 (2006.01)
G01F 1/00 (2006.01)

(52) U.S. Cl. .......................... 600/538; 73/861
(58) Field of Classification Search .......... 600/529–543, 600/300, 301, 484; 73/861
See application file for complete search history.

(56) References Cited

U.S. PATENT DOCUMENTS

| 4,796,639 | A | * | 1/1989 | Snow et al. | 600/532 |
| 5,137,026 | A | * | 8/1992 | Waterson et al. | 600/538 |
| 5,337,739 | A | * | 8/1994 | Lehman | 128/205.27 |
| 5,373,851 | A | | 12/1994 | Reinhold, Jr. et al. | |
| 5,490,502 | A | * | 2/1996 | Rapoport et al. | 128/204.23 |
| 5,501,231 | A | * | 3/1996 | Kaish | 600/538 |
| 5,518,002 | A | * | 5/1996 | Wolf et al. | 600/538 |
| 5,634,471 | A | * | 6/1997 | Fairfax et al. | 600/538 |
| 5,732,709 | A | | 3/1998 | Tacklind et al. | |
| 5,803,066 | A | * | 9/1998 | Rapoport et al. | 128/204.23 |
| 5,924,994 | A | * | 7/1999 | Harbrecht et al. | 600/532 |
| 5,984,872 | A | * | 11/1999 | Vriend | 600/529 |
| 6,019,731 | A | * | 2/2000 | Harbrecht et al. | 600/532 |
| 6,042,551 | A | * | 3/2000 | Harbrecht et al. | 600/532 |
| 6,190,326 | B1 | | 2/2001 | McKinnon et al. | |
| 6,283,923 | B1 | | 9/2001 | Finkelstein et al. | |
| 6,447,459 | B1 | | 9/2002 | Larom | |
| 6,468,222 | B1 | * | 10/2002 | Mault et al. | 600/531 |
| 6,579,242 | B2 | * | 6/2003 | Bui et al. | 600/537 |

(Continued)

FOREIGN PATENT DOCUMENTS

WO WO97/18753 5/1997
WO WO2004/027676 A2 4/2004

OTHER PUBLICATIONS

Boggs, et al., Peak Expiratory Flow Rate Control Chart in Asthema Care: Chart Construction and Use in Asthema Care, Annals of Allergy, Asthema and Immunology, vol. 81,Dec. 1998, pp. 552-562.

(Continued)

Primary Examiner — Charles A Marmor, II
Assistant Examiner — Navin Natnithithadha
(74) Attorney, Agent, or Firm — Brian K Johnson, Esq, LLC

(57) ABSTRACT

An enhanced electronic peak flow meter is provided that combines some of the enhanced electronic features found in other electronic peak flow meters with software for executing a stochastic process control and evaluating the digital respiratory data collected by the meter. The programmed stochastic process control is capable of selecting and calculating any one of a number of pulmonary function parameters including at least one statistical process control variable to determine a pulmonary threshold. Information systems linking doctor's offices and patient's meters are further provided to transmit warning data in cases where the pulmonary threshold is exceeded.

20 Claims, 5 Drawing Sheets

U.S. PATENT DOCUMENTS

| | | | |
|---|---|---|---|
| 6,824,520 B2 * | 11/2004 | Orr et al. | 600/529 |
| 7,118,536 B2 * | 10/2006 | Haberland et al. | 600/538 |
| 7,207,948 B2 * | 4/2007 | Coyle | 600/538 |
| 7,267,652 B2 * | 9/2007 | Coyle et al. | 600/538 |
| 7,438,686 B2 * | 10/2008 | Cho et al. | 600/484 |
| 2005/0133024 A1 | 6/2005 | Coifman | |
| 2007/0179347 A1 * | 8/2007 | Tarassenko et al. | 600/300 |

OTHER PUBLICATIONS

Global Initiative for Asthema (GINA), Global Strategy for Asthema Management Prevention, National Institute of Health, Bethesda, MD, National Heart, Lung and Blood Institute, NIH Pub. No. 02-3659, 2002.

* cited by examiner

APPARATUS AND METHOD FOR INTELLIGENT ELECTRONIC PEAK FLOW METERS

CROSS-REFERENCES TO RELATED APPLICATIONS

This application claims priority to pending U.S. Provisional Patent Application Ser. No. 60/662,605, filed Mar. 17, 2005 the entire contents of which are incorporated herein in its entirety.

Also informative and useful in understanding and applying the operation of the present invention, the following documents are also incorporated by reference in their entirety herein:

Global Initiative for Asthma (GINA), Global Strategy For Asthma Management And Prevention. National Institutes Of Health, Bethesda Md. USA, National Heart, Lung, and Blood Institute, NIH Publication No 02-3659, 2002; and Peak Expiratory Flow Rate Control Chart in Asthma Care: Chart Construction and use in Asthma Care, Peter B. Boggs, MD et al., Annals of Allergy, Asthma and Immunology, Vol. 81, Dec. 1998, pp. 552-562.

BACKGROUND

U.S. Pat. No. 6,447,459 (Larom) entitled Device and Method for Measuring Lung Performance, which is incorporated by reference herein in its entirety, allegedly discloses a sophisticated peak flow meter with certain mechanical enhancements that allow for more accurate measurements of certain respiratory functions. The enhancements are allegedly accomplished through novel techniques of dampening oscillations and eliminating the gravitational effects of the flow measurements taken by the device. See Abstract. As a result of the increased sensitivity of the peak flow meter and its respiratory measurement apparatus, more sophisticated and useful statistical measurements, such as one and six second Forced Expiratory Volume measurements (FEV1 and FEV6 respectively) are able to be measured. Further, Larom also allegedly discloses a coupling of the peak flow meter with a microprocessor and a non-volatile electronic memory such that the enhanced respiratory measurements taken by the device are transduced into an electronic format which are then stored in the memory for further transmission by the microprocessor. Larom further discloses a coupling of the microprocessor to any one of a number of warning indicators that may alert the user of a potential problem with the recorded respiratory function, such as the measured respiratory reading being outside a preprogrammed reference range. See Col. 11, l. 66 to Col. 12 l. 16. Such out-of range results may also be disclosed on an electronic display, viewable on the device, coupled to the microprocessor. The display of Larom also displays the enhanced measurements taken by the improved mechanical apparatus, such as FEV1 and FEV6, as well as other measurement calculated by the microprocessor, such a the ratio of FEV1/FEV6. See FIG. 17A and associated description. When coupled to a holding cradle coupled to a computer, Larom also allegedly discloses the transmission of the respiratory data to the computer such that the transmitted date may further be used to creation an electronic diary and/or be transmitted to a physician for interpretation of the measurements. See Col. 2, ll. 58-68 and Col. 13, ll. 1-19.

U.S. Pat. No. 6,190,326 (McKinnon) entitled Method and Apparatus for Obtaining Patient Respiratory Data, which is incorporated by reference herein in its entirety, allegedly discloses a component system for collecting patient respiratory information including a base unit and a removable mouthpiece. See Abstract. The mouthpiece allegedly includes electronic storage of identification information for a user of the mouthpiece as well as the respiratory measurements taken from the patient during testing. Such measurements may include FEV1 and Peak Expiratory Flow Rate (PEFR). The mouthpiece is coupled to a base unit which, in turn, may be coupled to a data network that transmits respiratory data recorded by the mouthpiece to an attending physician. Electronic display units may be included within the mouthpiece and base unit measurement system for displaying the respiratory data to the patient. Further, intelligent inhalers used for dispensing asthma medication may be coupled to the base unit such that the base unit records the date, time and amount of the medication dispensed by the intelligent inhaler. See Col. 7, ll. 35-57. Finally, the base unit is allegedly disclosed to include a patient performance manager in which treatment plans may be programmed by the attending physician either at the office or through the data network. See Col. 5, ll. 18-42.

Numerous other enhancements to inhalers or respiratory medication delivery devices are knows, such as those disclosed in U.S. patent application Ser. No. 10/997,278 having common inventorship with the present application, in which the delivery of the medicine is conditioned by the inspiratory flow sensors included on the medicine dispenser.

None of these devices have seen widespread clinical use, however, due to the large volume of raw data they provide. This data overload creates both a treatment dilemma and an associated potential liability for treating physicians. First, physicians do not have the time to review the large volumes of raw date that the all the electronic peak flow meters from all of their patients provide, whether presented as tabular pulmonary data or automatically charted for the ease of physician review. This is particularly true when considering the number of measurements performed per patient during a given monitoring period and the ease with which they may be transmitted over computer networks from home-based pulmonary detection apparatus, even if this only from a significant fraction of the number of asthmatics who by current disease management criteria might benefit from regular use of these devices. Further, health insurers have no current billing paradigm according to which physicians would be paid for their review of this data. This is particularly so in the absence of the following accompanying actions: face-to-face contact with the patient, a full review of the patient's history, an examination of the patient, a formulation of management options, a review of options with the patient or parent, instruction in the details of their implementation, and planning for reasonable ongoing monitoring and follow-up. Second, and more significantly, physicians and their insurers are reluctant to assume the risk of collecting patient data that their attending physicians do not have time to review fearing the liability of potential early warning signs within the unreviewed data, early warning signs that, in the worst case scenario, are indicative of a life threatening status.

Thus the need exists for incorporating certain analytic capacity directly into personal pulmonary function measuring devices, or their immediately accessible and attached equipment, to increase their ability to provide clinically useful information about the stability of and variations in various pulmonary function parameters. This is particularly valuable when the patient's data is monitored, recorded and analyzed regularly, over an extended period of time, i.e. over a monitoring period that would be unobtainable in the presence of a physician and including a significantly greater amount of data than that collected in the physician's office.

As an additional inventive aspect, the need exists for a programmable peak flow meter in which respiratory challenges, such as exposure to a particular asthmatic trigger, may be anticipated and peak flow meter programmed to take readings immediately in response to the trigger. In particular, a meter is needed that prompts for, anticipates and confirms a set of measurements taken without direct oversight by the evaluating physician, including the programming of options and algorithms to cover likely decision points needed by the physician. These would include intelligence within the peak flow meter that 1) prompts the user at appropriate time, such as at programmed intervals following an anticipated challenge, 2) has the ability to identify when users need to use rescue medications, and 3) changes the prompting algorithms to track response to rescue medications if the user indicates that such medications were used.

SUMMARY

According to one particularly preferred embodiment of the present invention an electronic peak flow meter including a sensor for measuring a respiratory airflow; a transducer for converting the respiratory air flow into an electronic value; a processor for storing the electronic value in a memory; a respiratory data section of the memory for storing a set of the converted electronic values; a program stored within the memory for execution by the processor, the processor executing the program to calculate at least one pulmonary function parameter from the set of electronic values and at least one statistical process control variable to determine a pulmonary threshold.

According to certain aspects of this preferred embodiment, a set of converted electronic values is taken over a sample period of time; the pulmonary function parameter is PEFR for each respiratory airflow and the statistic process control variable is a mean PEFR; and/or pulmonary threshold is three standard deviations of the PEFR for the respiratory airflows. According to or aspects of this preferred embodiment the pulmonary function parameter is FEV1 for each respiratory airflow and the statistic process control variable is a mean FEV1; the pulmonary threshold is 60% below the mean FEV1 and/or; the pulmonary threshold is updated by a health care professional based on an analysis of the calculated pulmonary function parameters and the calculated process control variables.

According to another particularly preferred embodiment of the present invention a system for evaluating respiratory air flow measurements is provided including an electronic peak flow meter having a sensor for measuring a respiratory airflow, a transducer for converting the respiratory air flow into an electronic value and a data port; a medical computer having a processor and a memory, the electronic value being stored in the memory, the medical computer also including a respiratory data section for storing a set of the converted electronic values, and a program stored within the memory for execution by the processor; and a computer network coupled to the data port and the medical computer wherein the processor executes the program to calculate at least one pulmonary function parameter from the set of electronic values and at least one statistic process control variable to determine a pulmonary threshold.

According to certain aspects of this preferred embodiment the set of respiratory data is taken over a sample period of time; the pulmonary function parameter is PEFR for each respiratory airflow and the statistic process control variable is a mean PEFR; and/or the pulmonary threshold is three standard deviations from the mean PEFR. According to or aspects of this preferred embodiment, the pulmonary function parameter is FEV1 for each respiratory airflow and the statistic process control variable is a mean FEV1; pulmonary threshold is at least eight consecutive converted data values outside of below the mean FEV1, all eight data values being on one side of the mean; and/or the pulmonary threshold is updated by a health care professional based on an analysis of the calculated pulmonary function parameters and the calculated process control variables.

According to a final particularly preferred embodiment of the present invention a method is provided for determining respiratory function including measuring a respiratory airflow; converting the respiratory air flow into a set of electronic values; storing the electronic values in a memory; calculating at least one at least one pulmonary function parameter from the set of the stored electronic values and at least one statistical process control variable from the pulmonary function parameter; and determining a pulmonary threshold.

According to particularly preferred aspects of this invention the method is performed repeatedly on a plurality of respiratory airflow samples and the step of storing includes the steps of testing the plurality of respiratory airflow samples and selecting an optimal respiratory airflow sample. According to or aspects of the method, pulmonary function parameter is PEFR and the at least one statistical process control variable is a mean PEFR and the pulmonary threshold is an associated standard deviation for the set of respiratory airflows. According to still or aspects of the method, the method includes step of determining a pulmonary threshold includes determining three standard deviations of the PEFR for the set of respiratory airflows. According to still or aspects of the invention the method includes step of issuing a warning alert when the pulmonary threshold is exceeded.

BRIEF DESCRIPTION OF THE DRAWINGS

A wide variety of potential practical and useful embodiments will be more readily understood through the following detailed description of certain exemplary embodiments, with reference to the accompanying exemplary drawings in which.

DEFINITIONS

Figure 1:
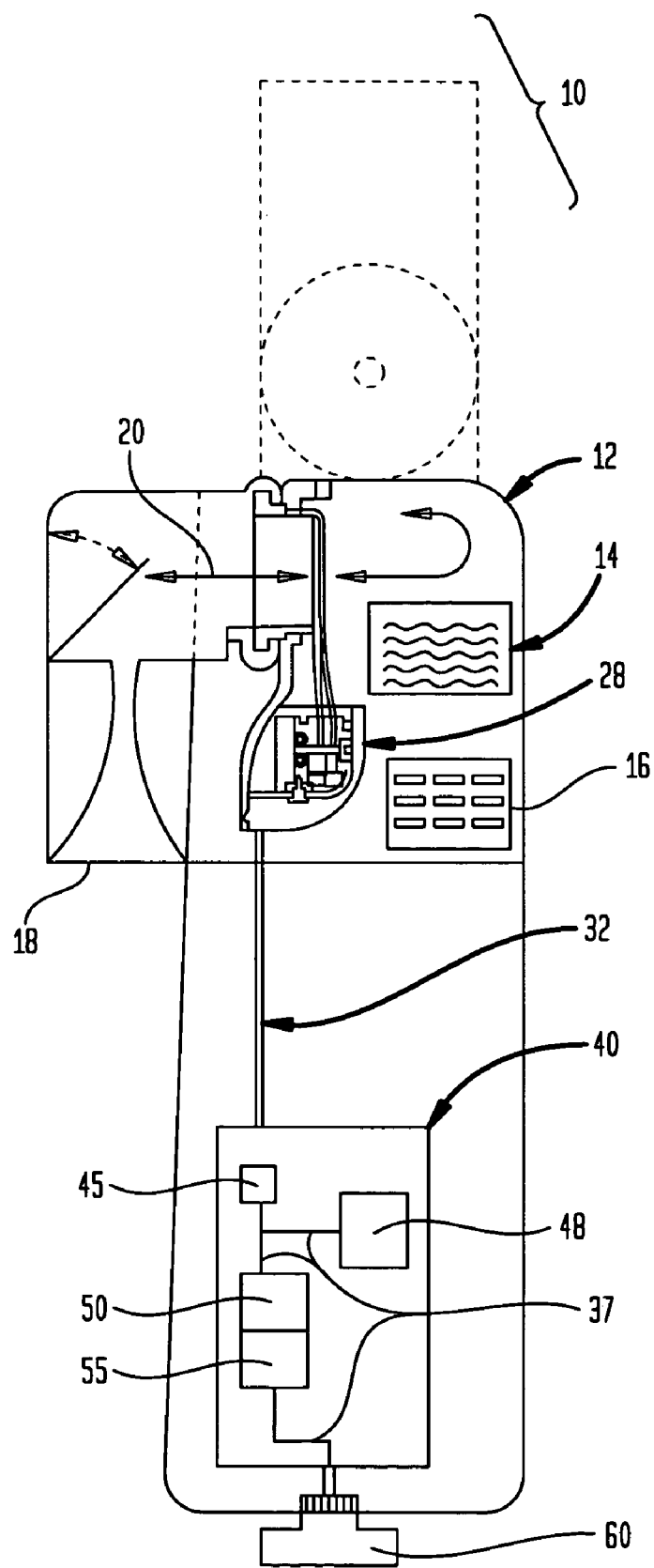
FIG. 1 is a side view of a peak flow meter (PFM) according to a particular preferred embodiment of the present invention.

When the following terms are used substantively herein, the accompanying definitions apply:

a—at least one.
activity—an action, act, step, and/or process or portion thereof.
adapted to—capable of performing a particular function.
and/or—either in conjunction with or in alternative to.
server—an information device, computer and/or a process running thereon that is communicatively coupled to a network and that is adapted to provide at least one service for at least one other device communicatively coupled to the network and/or for at least one process running on the other device.

associated—related to.

automatically—acting or operating in a manner essentially independent of external influence or control. For example, an automatic light switch can turn on upon "seeing" a person in its view, without the person manually operating the light switch.

bus—an electrical or electromagnetic connection that allows two or more data transmitting entities to be coupled so as to exchange information and data signals with one another.

can—is capable of, in at least some embodiments.

cause—to precipitate a result.

comprising—including but not limited to.

computer—any electronic device that accepts and processes data and information according to a set of instructions.

connect or couple—physically or logically link two or more entities.

data—distinct pieces of information, usually formatted in a special or predetermined way and/or organized to express concepts.

detect—sense or perceive.

determine—ascertain, obtain, and/or calculate.

execute—to carry out instructions.

indicate—to signify.

information—processed, stored, and/or transmitted data.

peak flow meter—any device capable of processing a user's respiratory information, such as any general purpose and/or special purpose inhaler, or other expiratory/inspiratory device for measuring lung performance.

initiate—begin.

instructions—directions adapted to perform a particular operation or function.

may—is allowed and/or permitted to, in at least some embodiments.

memory device—an apparatus capable of storing analog or digital information, such as instructions and/or data. Examples include a non-volatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory device can be coupled to a processor and/or can store instructions adapted to be executed by processor, such as according to an embodiment disclosed herein.

method—a process, procedure, and/or collection of related activities for accomplishing something.

network—a communicatively coupled plurality of nodes.

network interface—any device, system, or subsystem capable of coupling an information device to a network. For example, a network interface can be a telephone, cellular phone, cellular modem, telephone data modem, fax modem, wireless transceiver, Ethernet card, cable modem, digital subscriber line interface, bridge, hub, router, or other similar device.

notification—information transmitted to advise an entity of an event, status, or condition.

obtain—to procure and/or receive.

operation—a state of executing a predetermined plurality of machine-readable instructions.

plurality—the state of being plural and/or more than one.

predetermined—established in advance.

processor—a device and/or set of machine-readable instructions for performing one or more predetermined tasks. A processor can comprise any one or a combination of hardware, firmware, and/or software. A processor can utilize mechanical, pneumatic, hydraulic, electrical, magnetic, optical, informational, chemical, and/or biological principles, signals, and/or inputs to perform the task(s). In certain embodiments, a processor can act upon information by manipulating, analyzing, modifying, converting, transmitting the information for use by an executable procedure and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium IV series of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein.

provide—to furnish and/or supply.

provisioned profile—information indicative of desires and/or patient services associated with a medical entity.

proxy—an entity acting as a substitute for a separate and distinct entity.

receive—accept something provided and/or given.

register—(v) to identify a telecommunications device as communicatively coupled to a network.

registration—a status of a telecommunications device as being communicatively coupled to a network.

request—a message asking for something.

responsive—reacting to an influence and/or impetus.

sending—to convey.

set-up—initiated via at least one machine readable instruction.

signal—detectable transmitted energy that can be used to carry information. Operationally, a type of message, the text of which consists of one or more letters, words, characters, symbols, signal flags, visual displays, or special sounds, with prearranged meaning and which is conveyed or transmitted by visual, acoustical, or electrical means. The information in a signal can be, for example digitally encrypted via for example, public key, PGP, and/or triple-DES, etc. As another example, the signal can be broadcast via, for example, a spread-spectrum technology such as, for example a frequency hopping or a direct-sequence spread-spectrum system.

substantially—to a great extent or degree.

system—a collection of mechanisms, devices, data, and/or instructions, the collection designed to perform one or more specific functions.

telecommunications device—a product adaptable to communicate over a distance. For example, a telephone, fax machine, telex, networked information device, and/or cellular telephone, etc.

transmit—to convey (force or energy) from one part of a mechanism to another.

transducer—any of the various devices that convert or transmit energy from one system to another, often involving a conversion of one form of energy into another form of energy.

transceiver—any device that transmits and receives.

via—by way of and/or utilizing.

wireless—any data communication technique that utilizes electromagnetic waves emitted by an antenna to communicate data (i.e., via an unguided medium), including such data communication techniques as sonar, radio, cellular, cellular radio, digital cellular radio, ELF, LF, MF, HF, VHF, UHF, SHF, EHF, radar, microwave, satellite microwave, laser, infrared, etc. Wireless communications can include analog and/or digital data, signals, and/or transmissions.

Brief Medical Background

It should be recognized that the present medical state of the art regarding statistical process control program, including the associated pulmonary function parameters, statistical process control variables and the pulmonary thresholds, is in a developmental stage. The most significant work in this field has only been reported as recently as 1998 in an article entitled "Peak Expiratory Flow Rate Control Chart in Asthma Care: Chart Construction and use in Asthma Care" written by Boggs et al. and incorporated herein by reference (Boggs article). Those of skill in the art should realize that this field will continue to evolve and develop and that more sophisticated statistical control processes and associated variables are expected to be developed. Such statistical process control variables may include, but are not limited to. Natural Process Limits (e.g. UNPL—upper natural process limit and LNPL lower natural process limit), Sigma (standard deviation), X-Bar (average of serial function parameters during the observation period), URL (upper range limit) and mR-Bar (an average of serial differences during the observation period), all as described in Boggs. It is the intention of the present invention to be flexible enough to accommodate these advances, particularly as the technologies capable of being economically incorporated within PFMs advance to keep pace with the more advanced statistical processes. As such, the following discussion of the medical background, operational characteristics of the PFM and the specific following references regarding the adaptation of the PFM to Boggs statistical theories is only provided as an exemplary use of the invention given the current state of the medical arts.

Asthma is a chronic inflammatory disorder of the airways in which recurrent episodes of wheezing, breathlessness, chest tightness, and coughing are usually associated with widespread but variable airflow obstruction that is often reversible either spontaneously or with treatment. (Parts of this definition relevant to the present invention have been excerpted from the definition of asthma found in the article entitled: Global Initiative for Asthma (GINA), Global Strategy For Asthma Management And Prevention, National Institutes Of Health, Bethesda Md. USA, National Heart, Lung, and Blood Institute, NIH Publication No 02-3659, 2002) (GINA Strategy).

Optimal asthma management requires that treatment be adjusted to balance changes in activity of the inflammatory process and the airflow obstruction it causes. Some patients (or their parents if the patients are juveniles) have a sufficiently precise sense of changes in asthma activity to make appropriate treatment adjustments with relatively little external monitoring. Many patients, however, fare better with regular monitoring of various pulmonary function parameters as recommended in the above-mentioned GINA Strategy.

This GINA Strategy discusses the two time-honored methods of monitoring lung function. The first is spirometry, which is a process comprising the graphic representation of momentary and cumulative expiratory and inspiratory airflow over the course of a maximum respiratory effort. This is followed by a computation of a standardized set of pulmonary function parameters from either the graphic display or the data from which it was derived. Performance of a technically adequate spirometry test generally requires coaching by an experienced medical practitioner within a medical office setting. The medical diagnostic results of this test, which is usually performed on a periodic basis, is to monitor and record acute respiratory exacerbations over a long period of time (i.e. between office visits).

One of the pulmonary function parameters measured in the course of spirometry is the peak expiatory flow rate, or PEFR. This is the maximum rate of expiratory airflow achieved in the course of a maximal expiratory effort. Inexpensive mechanical devices capable of measuring PEFR with reasonable accuracy and reproducibility have been available for some time. PEFR is almost always achieved within the first half-second of a maximal expiratory effort, making the technically adequate recording of PEFR a relatively simple procedure that most patients can continue to perform reliably at home.

Current medical knowledge, however, shows that PEFR is not the pulmonary function parameter that has the best correlation with asthma activity, and it is possible for either errors in recording techniques or other respiratory conditions to confound the accuracy of PEFR measurements made with these relatively simple instruments. As stressed in the GINA Strategy, the economy, simplicity and reasonably good correlation with asthma activity of spriometry in most patients make their daily or regular use an extremely cost-effective way to track changes in asthma activity.

Some asthma patients have an innate sense of subtle changes in their own level of disease activity. These patients benefit relatively little from tracking of their asthma activity with these devices. Others have a very poor innate sense of early changes in their level of airflow obstruction, and can achieve much better control of their asthma if they use these devices regularly and have asthma management plans keyed to changes in home-measured peak expiratory flow rate (PEFR). Falling PEFR in general, and falling PEFR under specific circumstances (such as during an early morning measurement, after vigorous aerobic exercise, or during periods of increased allergen exposure), are often early warning signs of increasing asthma activity. The earlier warning provided by a fall in PEFR may be sufficient to significantly reduce the frequency of respiratory exacerbations in those patients who experience moderate to severe exacerbations in the absence of sufficient early clinical signs to initiate treatment changes in time to prevent the exacerbation.

As an additional medical consideration, while the raw data that can be recorded with existing electronic peak flow meters correlates well with risk of exacerbations, it does not correlate well with such quality-of-life indicators as patient-recorded symptom scores. The interpretation of this discordance that makes the most sense to us in that the airflow parameters recorded by these meters are primarily measures of large airway function while the primary locus of disease activity is in smaller airways, from which it does not "spill over" or extend to impair large airway function until long after it has achieved a sufficient level of activity to adversely impact quality of life.

The Boggs article reported an effort to improve the medical management of asthma by serially or periodically subjecting recent home-measured PEFR and FEV1 data to statistical process control analysis. These published case reports suggest that his recent retrospective identification of deviations in statistical process control comprise a more sensitive coupling of Boggs' measurements with disease activity as measured by qualify of life than what one can learn by simple inspection of raw data, i.e., are measured values above or below a selected warning threshold.

In response to this during recent years, rugged and reliable electronic peak flow meters have entered the marketplace at costs not significantly greater than those of mechanical meters. Some of these, such as that of Larom, claim to be capable of accurately measuring FEV1, defined as the volume of air exhaled in the first second of a maximal expiratory effort. Current medical knowledge seems to indicate that FEV1 correlates more closely with asthma activity than PEFR. However, performance of an accurate FEV1 measurement requires a sustained maximal expiratory effort of at least 1 second in duration, which is technically more demanding than the expiratory effort required for accurate measurement of PEFR. Nonetheless, it's a technique that most adults can also learn to perform reliably, at home, without medical supervision, and that many children can learn to perform reliably at home with parental supervision. Some of the existing electronic peak flow meters, such as Larom, have memory able to record and store a number of readings. Some of the existing electronic peak flow meters also have provisions for a physician's entry of modified treatment plan based on the data retrieved from the patient's devices by the doctors. See McKinnon.

While the technology is relatively new, electronic peak flow meters have not been designed to perform some of these more sophisticated respiratory data analyses that can enable and facilitate improved day-to-day asthma control. Implementation of these innovations on electronic peak flow meters is expected to enable the automated performance in backup software of a clinically useful long term tracking function for which automated tracking was not previously practical: The day-to-day benefits of the meter-based functions of this invention are expected to motivate enough patients to use their meters with enough regularity to for the first time generate enough data to make the long term tracking function practical.

In the remainder of this application, electronic peak flow meters incorporating one or more of the novel features of the present invention may be called "enhanced" electronic peak flow meters (EEPFMs).

DETAILED DESCRIPTION

FIG. 1 illustrates an electronically enhanced peak flow meter 10 (EEPFM) according to an exemplary embodiment of the present invention. The EEPFM accepts a user's respiratory input at opening 18, and channels it along pathway 20 to transducer 28. Transducer 28 converts the mechanical respiratory input into electronic from and transmits the corresponding electronic signals over communications bus 32 to electronics module 40. EEPFM 10 may also include display 14 for providing visual indications and results of a respiratory measurement and provide prompts to the patient during the use of the device. Finally, key entry pad 16 is provided on the EEPFM housing 12 for entering certain data associated with the respiratory testing such as, for example, date, time, or trial number.

Electronics module 40 is housed within EEPFM 10 and includes essential components according to one embodiment of the present invention. Electronics module 40 is coupled to communications bus 32 via its own internal communications busses 37. Electronics module 40 further includes a processor 45, internal processing circuitry 48, data memory 50 and stored program memory 55. Processing circuitry may comprise any of a variety of electronic circuitry that is used to process or convert the data from bus 32 into appropriate formats and values. In particular, processing circuitry may include digital signal processors (DSPs), attenuators/amplifiers, scalers, buffers and/or other data processing and storage electronics. Finally, attached to the housing 12 of the PFM 10, is an external date interface 60 that is coupled to the electronics module 40 and its associated components by internal communications buses 37.

Figure 2:
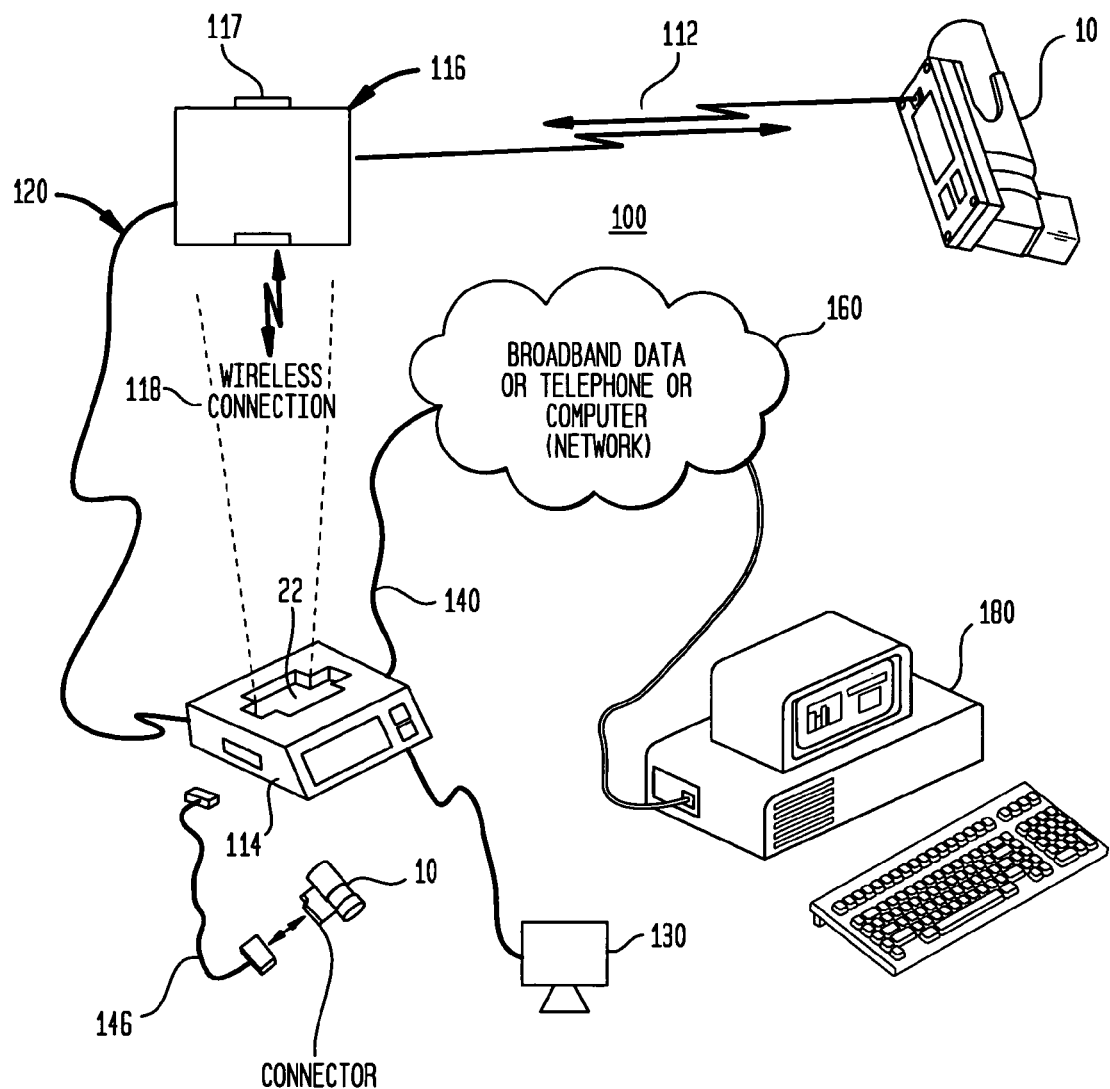
FIG. 2 is a data network system including peak flow meters of FIG. 1 according to a particular preferred embodiment of the present invention.

Referring to FIG. 2, a data network system 100 that includes the EEPFMs 10 of FIG. 1 is provided according to a particular preferred embodiment of the system. EEPFMs 10 are coupled to base stations 114 by any one of a number of presently known or heretofore developed data connection technologies. As shown in FIG. 2, EEPFM 10 (upper right) may be coupled via a wireless connection 112 to a wireless transceiver 116 which in turn is coupled to the base station 114 through either it's own wireless connection 118 or a dedicated, cable connection 120. Base station 114 is, in turn, coupled for data connectivity to a patient computer 130 which most desirably contains additional data and stored program memory that is coupled to its own processor via internal computer data busses. The base station 114 is either directly coupled via a data interface (not shown) to a data network 160 via a direct connection 140 or indirectly through patient computer 130 (not shown). Computers 180 at the office or hospital of the attending physician for the patient are also coupled to the data network via their own data interfaces.

Those of skill in the art will realize that the present invention and above-described EEPFM and associates system may be constructed of any of a variety of known components, containing known subparts thereof, so as to include the novel portions of the claimed apparatus and the to perform the novel portions of the methods according to the concepts of the present invention. In particular, any one of a number of known EEPFMs may be used to house the electronics module needed for this invention, including but not limited to those described in U.S. Pat. Nos. 6,447,459 and 6,190,326 as well as U.S. patent application Ser. No. 10/997,278. Also, any of the aforementioned data connection mechanisms may be interchanged or substituted so as to provide the necessary data connectivity used by the stochastic processes and associated hardware described in detail below. In addition, the electronic module containing the data memory and stored program memory may be located in other components of system 100 of FIG. 2 including being distributed among several components. Further, the present invention is not considered to be limited by ay particular composition of material that achieves the novel aspects of the present invention. For example, the EEPFM, computer, stored program and data memories may consist of any or all of RAM, ROM, volatile, non-volatile, FLASH or any other heretofore developed memory that is capable of storing the necessary data and executing the necessary program steps of the present invention.

According to one particular embodiment of the present invention, the EEPFM of FIG. 1 contains a statistical process control analysis program held in stored program memory 55 of EEPFM 10. To date, the price of computer memory has precluded the inclusion of a sufficient quantity of memory on a medical consumer good such as an EEPFM so as to permit the storage of complex statistical analysis programs as well as the volumes of accompanying data memory on which the programs operate. Further, to date, the computational resources and accompanying energy requirements for the processors performing statistical analysis on the patient's collected respiratory data have precluded the incorporation of such components into relatively cheap EEPFMs.

Figure 3:
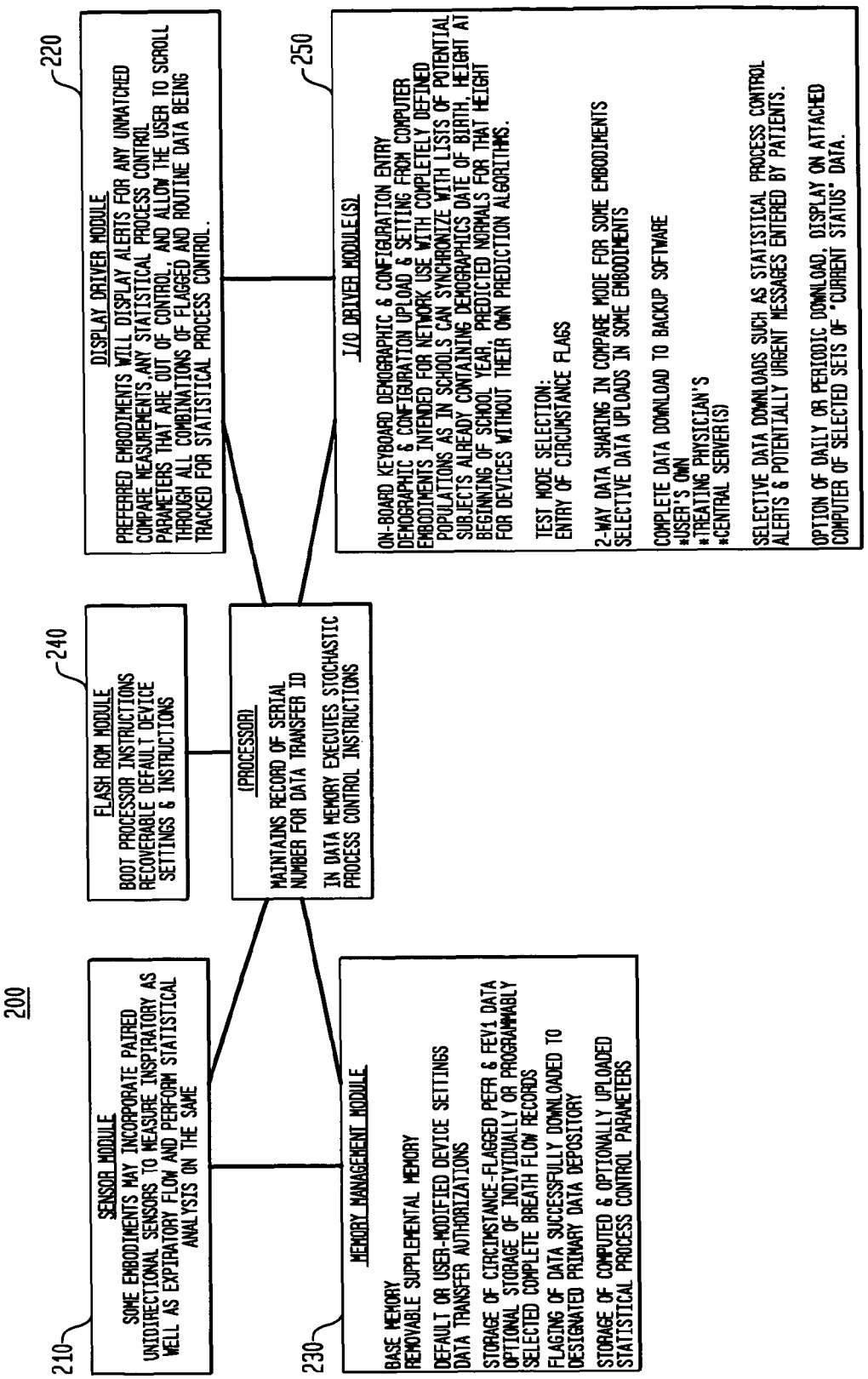
FIG. 3 is a software architecture for the statistical process control software according a particular preferred embodiment of the present invention.

FIG. 3 illustrates exemplary software architecture for the statistical process control program according to one embodiment of the present invention. The various software modules that constitute the entire software program 200 stored within the stored program memory 55 of EEPFM 10 are graphically illustrated as loosely interconnected functional blocks with exemplary functions being performed by each module as illustrated within those blocks. It should be recognized by those skilled in the art that the novel aspects of this invention are program independent such that the software source code may be written in any particular programming language, e.g. C, C++, Fortran, Pascal, JAVA, and may even include open source programming components.

Referring again to FIG. 3, the statistical process control program of the present invention includes a sensor module 210 for sensing, adjusting and manipulating the transducer 28, and optionally other electronically controlled mechanical components within the airflow chamber of EEPFM 10, all in response to control signals passed by the processor along communications bus 32. These adjustments may be conditioned upon a number of different criteria such as, for example, the number of times the PFM is used, the times of day during which it is used, the results of the last few respiratory readings taken or any other desirable control aspects of the sample data or the operation of the statistical process control program. Further, the sensor software module may pass data to the display module 220 for displaying failures in the sensors or for indicating a proper respiratory reading being taken (possibly as aided by the processor under control of the statistical process control program).

Referring again to FIG. 3, the statistical process control program includes a memory management module 230 that operates to ensure the integrity of the data in the memory, periodic replacement algorithms related to the memory contents, methods of marking respiratory data for later identification (e.g. time and date stamps or flagging of data for download to the physician's office) as well as a myriad of other data related functions. Also within the memory related portions of the statistical process control program is the ROM module 240 that contains the "boot code" for initializing the processor and the establishment of the software operation for all other software modules.

Also included within statistical process control program are the display software module 220 and the I/O software module 250. The display software module 220 is responsible for all display drivers for visual and audible alarms on the EEPFM including any displays for incorrect respiratory measurements and paged data displays of the respiratory data stored in memory for perception, selection and manipulation by the patient. Finally the I/O software module includes drivers and software for operation of the data interface 60 on the EEPFM including the scheduling of data uploads to the patient computer 130, the doctor's computer 180. In addition, the I/O software module handles the input from the key entry pad 16 of the EEPFM 10 and supplies the data so entered to the processor and the memory management module for further processing and storage. Further, according to a particularly preferred embodiment of the present invention, data and software downloads from the patient computer 130 and the doctor's computer 180 to the EEPFM may be coordinated with the I/O software module including automated data downloads, revised statistical process control alerts and new process control parameters. Also, critical readings under the control of the processor may be immediately transferred through the I/O software module to the doctor's computer for alert notification of a medical emergency concerning a respiratory reading.

Figure 4:
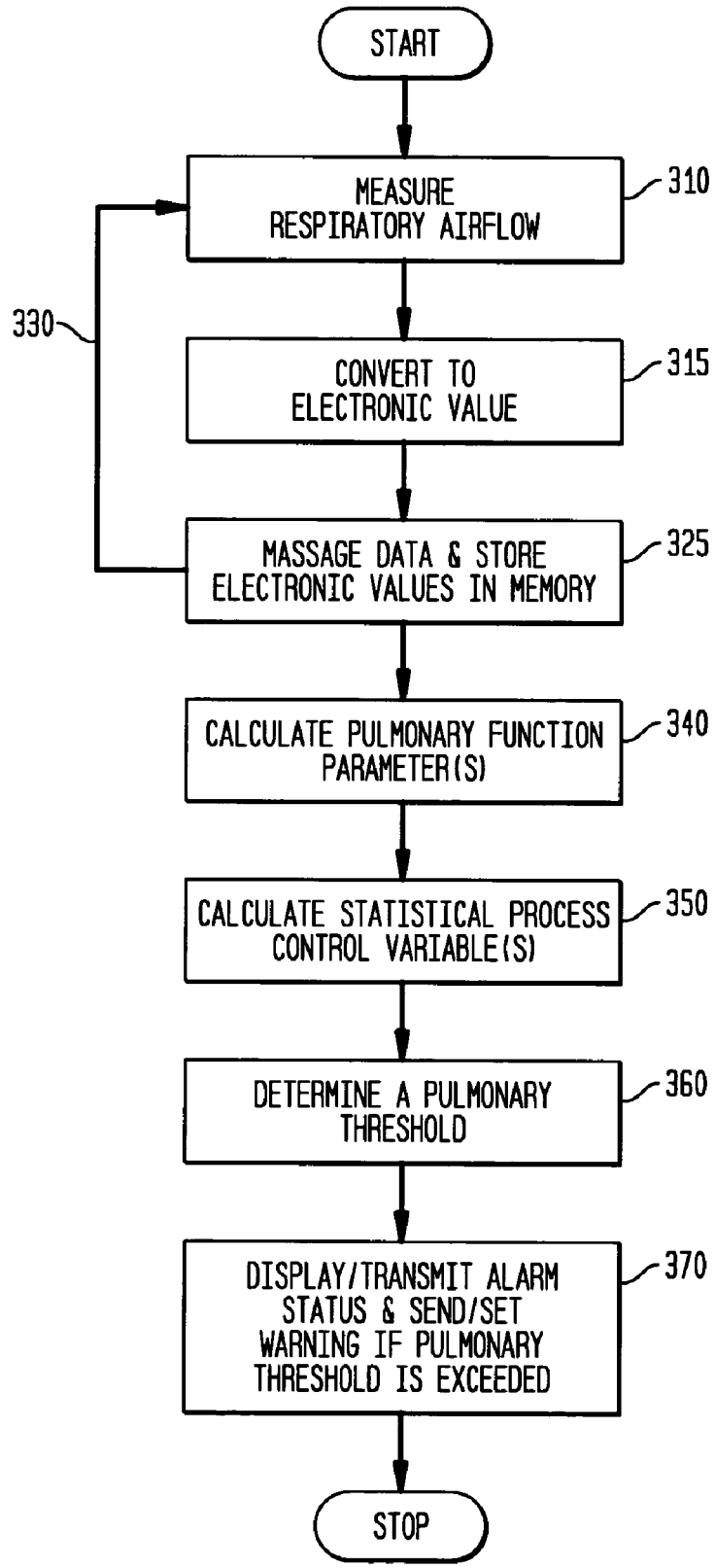
FIG. 4 is a flow diagram for taking respiratory measurements according to a preferred embodiment of the present invention.

FIG. 4 provides one particular method according to which the statistical process control program is used to operate on the accompanying respiratory data. At step 310 the patient blows (or inhales) into opening 18 of EEPFM 10 and that forced respiration travels along pathway 20 to transducer 28. At step 315, the transducer converts the mechanical airflow into electronic signals which travel along bus 32 to electronics module 40. At step 325, the processor 45, possibly with the assistance of the processing circuitry 48, massages the data and stores it in data memory 50 for later processing by the statistical process control program. This portion of the process, including the measurement of the respiratory airflow, conversion by the transducer and storage of the electronic values in memory, may occur repeatedly according to repeat loop 330 and the need for repeated measurement as provided in detail below.

Following the storage of a statistically significant data set for respiratory measurements, at step 340 of FIG. 4 the statistical process program stored in stored program memory 55 operates on the data to calculate certain pulmonary function parameters. According to current medical practices regarding the treatment of asthma and other respiratory ailments, as discussed in detail below, a key pulmonary function parameter to be calculated is the peak expiratory flow rate (PEFR). This is the maximum rate of expiratory airflow achieved in the course of a maximal expiratory effort. Other more advanced expiratory flow rates, such as FEV1—the volume of air exhaled in the first second of a maximal expiratory effort— may also be calculated by the statistical flow program from the respiratory data within the data memory.

At step 350 statistical process control variables are calculated by the processor 45, possibly in conjunction with the processing circuitry 48, according to the particular statistical process control program being executed. In particular, if PEFR is being measured and used to diagnose a patient's respiratory capacity, then a mean PEFR over a certain statistically significant period of time may be calculated for further analysis. If the pulmonary function parameter to be measured is FEV1, then the statistical process control variable may also be a mean FEV1 over a certain statistically significant period of time.

At step 360 of FIG. 4, the statistical process control program calculates a pulmonary threshold associated with the appropriate statistical process control variable for a given pulmonary function parameter. From a medical standpoint, as described in more detail below, this pulmonary threshold is likely to vary on a patient-by-patient basis, given each patient's particular medical circumstances as evaluated by the patient's physician. In certain statistical models, a first approach pulmonary threshold may be determined by the statistical process control software. This value may then be updated by the analysis of the statistical process in response to the respiratory data collected. In sum, the pulmonary threshold may vary over time or according to different environmental circumstances experienced by the patient or, for example, in response to a serious degradation of a patient's pulmonary capacity. As purely hypothetical examples of any particular patients' circumstances, a potential pulmonary threshold for PEFR may be set to be three standard deviations of the mean PEFR (the statistical process control variable). Likewise, a potential pulmonary threshold for FEV1 may be set to be 60% below the mean FEV1 (the statistical process control variable). In any case, however, the pulmonary threshold is a value that is associated with the statistical process control variable and pulmonary function parameter under the control of the statistical process control program. Whether determined a priori as a "first choice" or default of the statistical program control or whether subjectively set by the attendant physician based on an analysis of the patient's data, the pulmonary threshold indicates a potentially severe patient condition. As such, the process shown in FIG. 4 ends with an alarm display step 370 and possible transmission of the alarming condition the doctor's office indicating the alarm condition.

Statistical Process Controls and Examples of Use

One of the complications in the application of the present invention is that it is based on an analysis of medical data using technology that has heretofore not been incorporated into EEPRMs. By the very nature of statistical process control, the present invention's most accurate medical use and most economical commercial use will ultimately be determined by the massive quantity of empirical data generated by the plurality of users that use, record and analyze their respiratory functions with such devices. Thus, the clinical operation of the present invention, including the selection of appropriate statistical control variables and the EEPFM's various bells and whistles, will be provided by way of example.

Invention Application #1.

Numerous uses of the present invention are described in the following discussion. The first might be called, "Personal pulmonary function measuring devices to perform programmed analysis of "trends and patterns." The enhancements of electronic peak flow meter function that comprise this invention will individually and collectively enable electronic peak flow meters to perform analytic functions, facilitate diagnosis and guide care in ways that do not require the specific input and updating of instructions from treating physicians. These features are necessary for both electronic and mechanical peak flow meters that lack the enhancements of the present invention. The concept of incorporating statistical process control analysis into electronic peak flow meters may be novel, but medical research can not predict the optimal default selections for circumstances to be chosen for analysis or the optimal choice of analysis interval and alert thresholds until thousands of the EEPRMs in the public domain and their data and accompanying clinical correlates have been collected for factor and subgroup analysis.

Selection of pulmonary function parameters for analysis.

Almost all adults, and children age greater than or equal to 5 with adult supervision, can learn to perform reliable, technically adequate measurements of peak expiratory flow rate (PEFR) after simple initial instruction. Most such individuals can master the slightly more demanding maneuver for measurement of one second forced expiratory capacity (FEV1) and perform it without medical supervision with nearly the same reliability. Methods exists to identify common patterns of technically inadequate tests for FEV1, and software has already been incorporated into some electronic peak flow meters that also measure FEV1. See Larom. Nonetheless, there are other pulmonary function parameters for which the tracking of daily home measurements might be clinically useful, but the respiratory maneuvers needed for their measurement are more technically demanding and for this reason are generally only performed under medical supervision. It is the purpose of the present invention to be applicable to the measurement of those additional pulmonary function parameters for which tracking may be clinically useful.

One enhancement of this invention is the incorporation of real time, semi-automatic statistical process control analysis of serially collected pulmonary function measurements to trigger alerts based on deviations from statistical process control. This provides a much more sensitive and specific measurement of asthma control and earlier identification of deteriorating respiratory control than any possible set of specific numeric alert threshold values. Further, such measurement eliminates the need for physician selection and periodic updating of numeric alert thresholds. Clinical trials will be needed to identify those sets of statistical process control alert parameters that optimally balance sensitivity and specificity for most patients. Once these have been determined, however, the vast majority of asthma patients will be able to achieve efficient, cost-effective monitoring of asthma control with the EEPFM device as it comes out of the box. It is expected that there will probably be a subset of asthma patients who can achieve better control with individually optimized statistical process control alert parameters than whatever set of parameters are selected as default settings. Once individual statistical process control parameters are optimized for an individual patient, however, they should rarely if ever require updating.

This statistical process control analysis feature of the present invention is described as "semi-automatic" rather than fully automatic. This is because for optimal precision and efficiency, statistical process control must be performed on relevant sets of data. Pulmonary function in asthma is generally lower upon waking from sleep than when measured during the patient's biological afternoon or evening. The principal subsets for statistical process control analysis will be serially recorded during routine daily morning (AM) and evening (PM) measurements, but statistical process control analysis will also be performed on data meeting other criteria and combinations of criteria, particularly when there are sufficient numbers of measurements in those data sets. Thus, it will be necessary to indicate which measurements are routine daily AM measurements, which are routine daily PM measurements, which are routine AM or PM measurements to which other circumstances such as the presence of specific respiratory symptoms also apply, and which measurements are exclusively for other circumstances and should not be included in the statistical process control data sets for routine AM and PM measurements. As is already the case with many unenhanced electronic peak flow meters, EEPFMs will have date and time entry fields and internal clocks and calendars capable of date and time stamping all meter readings (tests).

To minimize the number of data entry steps for the user to accurately record the circumstances of each measurement, preferred embodiments of this feature of the invention will have data storage set assigned in the data memory 50 for entry of the patient's usual waking and bedtime hours. In the absence of other specification of circumstance, readings taken from 3 hours before to 3 hrs after the specified waking hour (or other specified intervals) may be presumptively assigned to be routine AM readings. In the absence of other specification of circumstance, readings taken between the end of the presumptive AM interval as defined above and one hour after the specified usual hour for going to bed (or any other time bracket that may be determined to be more effective for either an individual patient or to be a general default setting for most patients) may be presumptively assigned to be routine PM readings. Patients whose day-night schedule changes in comparison to clock time because of shift work or for other reasons may in some embodiments have the option to enter different sets of bedtime and waking hours and change between them as schedules cycle. This use of presumptive routine AM and PM test assignments will give users the option to override or supplement presumptive assignments. A supplemental data entry could be to note that a measurement is a routine AM reading but that respiratory symptom(s) or the specific symptom of cough are also present. Most asthma patients will not normally have occasion to use their peak flow meters at night (during normal sleeping time) in the absence of circumstances that should be specified for optimally efficient tracking. In fact, many users will not take the time to enter non-default circumstance data, particularly if they wake up at night with symptoms, and fall back to sleep after using their EEPFM before and possibly again after taking a treatment. To accommodate these common behavior patterns, certain programmed cycles may be used within the present invention such that presumptive circumstance assignment based on time may presumptively assign the circumstance of "night" to readings taken between the end of the "routine PM" time window and the beginning of the "routine AM" interval. Embodiments of enhanced electronic peak flow meters with this feature may be shipped with default configuration settings to perform statistical process control analysis of both the frequency distribution of readings taken at night and of the numerical values of nighttime PEFR and FEV1. Users would then be encouraged to report other circumstances associated with meter readings taken at any hour of the day, such as presence of cough and/or wheeze, or a measurement taken to document response to rescue inhaler. However, it is anticipated that because of the tendency of people who wake during the night because of respiratory symptoms to be more interested in getting back to sleep than in documenting circumstances, statistical process control analysis of these two parameters of nocturnal asthma activity may be the most pragmatic way to track this aspect of the disease. Statistical process control analysis of all "night" readings and of the frequency of "night" readings may also be the most practical way to track nocturnal disease activity in patients who do take the time to enter other features of their nocturnal symptoms, as if no single combination occurs with sufficient frequency for statistical process control analysis, the global category of readings taken at night may still give the best results.

Experience from clinical trials should identify the types of circumstance for which tracking readings for statistical process control analysis is clinically useful. Further, the clinical trials should also identify, when as a default parameters to track readings for all users, when to track users meeting certain demographic criteria (such as children below a certain age, for example) and when to track patients with specific clinical features. In each case, the tracking of readings taken under different circumstances or sets of circumstances for statistical process control analysis can be turned on or off using the key entry pad 16 in the configuration setting of the EEPFM. Other preferred embodiments of enhanced electronic peak flow meters will also allow the definition of additional, user-specific conditions for tracking for statistical process control analysis. Examples could include readings taken during or immediately following exposure to smoke or chemical vapors at work, and readings taken under the same circumstances when the patient is experiencing increased respiratory symptoms.

Readings taken under conditions that meet more than one circumstance classification may be included in the statistical process control analysis data sets for each individual circumstance and each possible combination. Thus, a routine AM measurement taken at a time when the patient is experiencing any respiratory symptom, when the symptoms include cough, when he believes he has a cold or other respiratory infection and when he is experiencing nose and/or sinus symptoms may be included in the following data sets for statistical process control analysis: Routine AM readings, readings taken in the presence of any lower respiratory symptom, readings taken in the presence of the specific lower respiratory symptom of cough, readings taken in the presence of a cold or respiratory infection, readings taken in the presence of increased nasal or sinus symptoms, and all possible combinations. Once again, the availability of EEPFMs capable of statistical process control analysis will generate an unprecedented wealth of data for this analysis, and only experience will determine the relative clinical usefulness of various subsets and combinations and the patient populations for which they have value. For example, some users will have unique, user-specific sets of circumstances for which tracking and statistical process control of pulmonary function may be clinically relevant, and facilitate improved disease control, preferred embodiments of this invention will allow the definition of individually relevant circumstances or sets of circumstances for pulmonary function tracking and statistical process control analysis.

Some sets of circumstances for which statistical process control analysis may be clinically relevant may occur with sufficiently low frequency that it may not be practical to store enough historical data in the data memory 50 of the EEPFM for statistical process control analysis. Some embodiments of this feature of the invention may allow the computation of statistical process control parameters in backup software for data collection circumstances. When sufficient data resides in the computer but not on the device statistical process control may be performed on the backup data device and transmitted back to the EEPFM for these circumstances and sets of circumstances, so that the device can give alert messages for loss of statistical process control for readings taken under these specific circumstances.

An example of the previous scenario may involve a cat-allergic child whose family visits Grandma each for Thanksgiving. Although the family stays in a motel so the child doesn't have to sleep in the same house with Grandma's 3 cats, the family would presumably attempt to spend as much of the weekend as tolerated at Grandma's with the rest of the family. The child's PEFR and FEV1 may always trigger alert messages during these visits, and they may usually be fairly well controlled by "usual" increases in medication use. A Friday night or Saturday AM reading outside of the statistical process control range for readings taken during the infrequent but medically critical special circumstance of visiting Grandma and the cats may still be a clinically important warning to begin a steroid burst and may be identified by the EEPFM as a caution such that the child refrains from returning to the house with the cats.

For instances like this example, when some of the prior readings used to perform statistical process control calculations may be old enough that a child patient may have grown in the interim, embodiments of the meter that incorporate software to calculate predicted values of PEFR and FEV1 may perform statistical process control calculations with all values expressed as percent of predicted. Embodiments of the meter that do not contain predicted value calculation software may adjust for growth by converting absolute measured values of PEFR and FEV1 recorded under that circumstance into the ratio of the absolute measured value to the mean value of routine same time (AM or PM) measurements of the same parameter (PEFR or FEV1) on occasions when no special circumstance was flagged, from 15 or 30 days before to 15 or 30 days after the date of that reading.

Another application of the alarm feature of the present invention is directed to the remote alerting of treating physicians who want a simple, efficient, easy-to-process warning when their patients are beginning to drift out of control, without being inundated by extraordinary amounts of patient pulmonary function data. The present invention as provide in the system of FIG. 2 is designed to encompass this aspect in that the EEPFM will transmit such notices to the doctor's office computer through the data network 160 when such alarms occur. It should be realized that the interface to the data network may be as simple as a telephone modem connection with either toll-free dial-up access to a server or dial-up access to the internet, or with software emulations of such devices on a patient's or his/her family's computer. For this application, the enhanced electronic peak flow meter does not send raw pulmonary function data but rather transmits the statistical process control variables. Patients may, of course, send this data at any time but should be prompted to do so by the memory management module 230 of the software when the EEPFM data memory 50 approaches full capacity. Various memory management schemes may be used, such as first-in-first-out (FIFO) in the absence of a data transfer to preserve the most recent or otherwise relevant data. Alternatively, the statistical process control software may selectively discard the most statistically insignificant data to preserve room when the data memory 50 reached capacity. When and if the patient drifts out of statistical process control for either AM or PM readings, the EEPFM may also be programmed to prompt the patient to download data simply to establish connection to the base station 114, even if the data memory has not reached capacity, so that alert messages may be displayed for the patient or parent via transmission of the alert to the patient computer, while also sending the alert message to the treating physician.

In an unenhanced peak flow meter, which only displays alert warnings if single measurements fall below designated thresholds, letting a curious child blow into the meter or another person with asthma measure his or her own peak flow and/or FEV1 will have no impact on the meter's subsequent performance for its primary user. Inclusion of spurious measurements into data sets forming the basis for statistical process control analysis, however, will confound the statistical process control analysis to a variable degree. Enhanced electronic peak flow meters incorporating the feature of statistical process control analysis should therefore have the option, either before or after a measurement is taken, to identify that reading as for a guest user, excluding that reading from the data set used for statistical process control analysis for the primary user. Such a user selection could be made available through the key entry pad of the EEPFM. In other more versatile embodiments of this invention, the EEPFM may allow for the following additional multiple user features: tagging of measurements for multiple guest users; allowing individual guest users to designate usual sleep and wake times; performing statistical process control analysis of their data if they make sufficient use of that meter; allowing the guest user data to be exported to their own meter(s) and backup software; and allowing the importation of data to the device and/or its backup software in the event that the primary user records data as a guest on a different device of the same kind.

Further to other inventive aspects of the present invention, if at least a portion of the stored program memory 55 of the EEPFMs are constructed with reprogrammable flash memory, improved statistical control software can be uploaded to the devices when the devices are connected to the doctor's office 180 or the patient computer 130. Updated software can also be programmed into units that have not yet been sold, so they will continue to work when first taken "out-of-the-box,", but they will work better with improved software based on accumulated data analysis. Further, the initial run of meters can have default settings to use the same two week analysis interval and the same circumstances of analysis (separate analysis of AM and PM measurements), and the same parameters and settings used in the Boggs Article. The same default settings can be used for statistical process control analysis of FEV1. As noted above, it is expected that updated software can be uploaded as it is developed. If users enter demographic and medication use data, these features will encourage patients to use the device as their personal data assistant for asthma. As a further benefit to the device manufacturers, download patient data to the manufacturer's website on a regular basis may be used to take advantage of an offer of free long term tracking with notification of deviations from control that occur over too long a time frame to be picked up by the meter, over time the manufacturer acquire the data to determine whether different statistical process control parameters than those used by Boggs might be more efficient as new "default" settings.

Recording of additional pulmonary function parameters for this application of the present invention.

It is proposed that for the recommendation of regular twice daily home use, the selection of pulmonary function parameters for recording and tracking be limited to those not requiring a forced expiratory effort greater than 1 second in duration, as a 1 second maximal expiration yields data that correlates well with asthma activity. It is believed that most patients would find the more demanding respiratory efforts needed for the measurement of additional pulmonary function parameters to be sufficiently burdensome such that by asking them to take respiratory measurements as often as statistically desirable to record PEFR and FEV1, overall meter use would fall resulting in sloppy technical performance and poor data quality. This is not the case for simple pulmonary stress testing as an adjunct to cardiac stress testing, however. This is a much less frequently performed study in which the examining practitioner does whatever is practical to minimize the collection of confounded data, such as the repetition of a post-exercise reading would require complete repetition of the costly, time-consuming and not entirely risk-free cardiac stress test procedure.

Coaching of test subjects to achieve accurate maximal respiratory effort is also important to minimize confusing data. As appropriately coached maximal respiratory efforts are more likely to result in more accurate data for automated screening and in a lower frequency of uninterpretable data in tests requiring remote interpretation by a respiratory specialist, it is recommend that the cardiac stress test laboratory personnel administering pulmonary function tests with appropriate embodiments of EEPFM have training and periodic refreshers in patient coaching for these tests. (This training need not require live human instructors.)

PEFR is a less precise measure of asthma activity than FEV1 and has not been validated as a surrogate for FEV1 in cardiopulmonary stress testing. It is proposed that PEFR is tracked as well as FEV1 in a preferred embodiment of this invention. However, PEFR as percent of predicted and pre-to-post-challenge changes in PEFR should approximate the same percent of predicted and changes in FEV1 for airflow obstruction caused by asthma. Discordance between percent predicted and pre-to-post-exercise changes in PEFR and FEV1 should help off-site interpreters differentiate irritant and other non-asthmatic factors from asthma as causes of exercise-associated symptoms and pulmonary function changes.

While FEV1 is the standard for measurement of simple pulmonary challenge response, the recording of additional pulmonary function data will aid interpretation and facilitate the recognition of non-asthmatic factors that could confound interpretations based simply on pre to post test changes in FEV1. When patients are coached by trained technical or nursing staff, it becomes reasonable to ask them to perform complete maximal forced expiratory maneuvers, to maximize the precision and interpretability of the resulting pulmonary stress test data. Preferred embodiments of EEPFM may therefore include areas within data memory 50 for the recording of total forced vital capacity (FVC) or 6 second vital capacity (FEV6) (an electronically easier-to-measure parameter that is a reasonable surrogate for FVC in almost all patients except those with severe emphysema or chronic obstructive pulmonary disease (COPD)). Sufficient data memory to record the data needed to produce standard flow-volume and volume-time displays of all test breaths should be available if desired by the interpreting respiratory specialist to aid in test interpretation.

As abnormalities in the inspiratory flow loop are strong indicators of probable confounding of pulmonary function data by non-asthma irritant factors, further preferred embodiments of the present invention will incorporate the recording of inspiratory as well as expiratory flow data. This will pose different technical requirements for electronic peak flow meters utilizing different flow-sensing mechanisms. Some flow sensors are bidirectional, in which case design optimization for cardiopulmonary stress test use can be achieved by configuring the processor to record inspiratory as well as expiratory flow data. For devices utilizing unidirectional flow sensors, design optimization for cardiopulmonary stress testing will require the construction of a separate device incorporating two flow sensors, positioned for the separate measurement of expiratory and inspiratory airflow.

Invention feature of tracking percent of technically satisfactory expiratory efforts for measurement of FEV1, and prompting users when to change primary output variable between PEFR and FEV1.

Almost any forced expiratory effort can produce a technically valid measurement of PEFR. Clinical experience has adopted the consistency standard of the best of three consecutive readings for which the second-best is within 50 liters per minute of the best. A technically valid measurement of FEV1 requires a rapid acceleration of expiratory flow rate to maximal at the beginning of the expiratory effort, and sustained maximal expiration for at least one second. For some young children, loss of the ability to perform a technically adequate FEV1 maneuver, measurable as in increase in the frequency of technically unsatisfactory efforts while they continue to meet the consistency standard for PEFR, is a variable that correlates with asthma activity. The American Thoracic Society standard for office spirometry specifies up to 8 attempts to perform a technically satisfactory maneuver and the Society does not endorse comparison with predicted normal values for patients who fail to provide technically adequate breaths. However, real world patients performing unsupervised or parentally supervised measurements of PEFR and FEV1 at home, especially children and especially when expected to take readings twice every day, day in and day out, may not always perform respiratory maneuvers that meet the ATS standard and may tire or refuse to perform up to 8 attempts to achieve consistent, technically satisfactory readings.

These characteristics of children in general and of children with asthma can be accommodated by enhanced electronic peak flow meters with the feature of this invention of allowing device configurations to either record or not record technically inadequate measurements of FEV1 from breaths that meet the PEFR standard for consistency (the PEFR consistency standard excluding breaths with coughs that can artificially increase PEFR and decrease FEV1) and to perform statistical process control and comparison analyses for FEV1 using only breaths that meet the FEV1 technical adequacy standard, or to separately analyze all breaths and the subset of breaths meeting the FEV1 standard for technical adequacy.

If FEV1 is selected as the primary tracking variable for single patient use, office spirometry standards would result in the user being prompted to blow again until he or she achieves either three technically satisfactory recordings of FEV1 or 8 attempts have been made. A relaxed FEV1 standard would prompt until two technically satisfactory readings have been obtained in a minimum of 3 attempts, or, for routine daily measurements but not for comparison measurements, one technically satisfactory reading in 5 to 8 attempts. If PEFR is selected as the primary tracking variable, the user would be prompted to record another blow until three blows have been recorded for which the best two values of PEFR are within 50 liters per minute of each other. Experience will determine which of these standards is more practical as a default setting for users of different ages. Because of the variability between individual patients, and of many child patients over time, this invention includes the optional feature of tracking the percent of breaths which meet the ATS standard for measurement of FEV1, and prompting the user or the user's physician to switch between standards based on percent technically satisfactory and unsatisfactory breaths for measurement of FEV1.

Saved PEFR and FEV1 values for statistical process control analysis may be a single "best" value from the set of 3 or more breaths comprising each test. While some embodiments of enhanced electronic peak flow meters may allow other "best" value selection options in the configuration menu intended for treating physicians, it is anticipated that when the primary output variable is assigned to be PEFR, the test selected as "best" will be the breath with the highest value of PEFR for which the $2^{nd}$ highest value is within 50 liters per minute. When the primary output variable is assigned to be FEV1, if the device has been configured to save and track only FEV1 from breaths that meet the ATS criteria for technical accuracy, the test selected as "best" will be the breath meeting this ATS standard with the highest numerical value for FEV1. If the device has been configured to save and track the best FEV1 irrespective of whether that breath meets the ATS standard for technical accuracy, the test selected as "best" will the test with the highest numerical value of FEV1, regardless of whether it meets the ATS standard for technical accuracy.

The operation of calculating the percent of breaths meeting the ATS specification for technically accuracy of FEV1 will count that percent for all breaths recorded by that individual that are not deleted or designated as user error, not just the "best" breath saved as the breath of record for each test, during a rolling time interval.

In certain conditions of non-asthmatic increased airway irritability, which not infrequently co-exist with asthma, blowing harder increases the amount of irritant change in the breath pattern. The patient typically feels the same irritation as discomfort in the throat or chest with increasing respiratory effort, and may hold back from maximal effort because it hurts to blow all out. In this condition, which can confound the tracking of asthma if it isn't recognized, holding back from maximal respiratory effort may result in a breath pattern with zero or minimal irritant effect while a truly maximal respiratory effort, giving higher numerical values for both FEV1 and PEFR, increases the amount of irritant change in the recorded breath pattern. For strong enough breaths may these irritant changes may cause failure to meet the ATS standard.

The natural tendency of patients to hold back from maximal respiratory effort in this condition is not constant over time, i.e., affected patients will not reproducibly blow at 85% or 90% of maximal capacity. This phenomenon can thus introduce a non-asthmatic source of variability into serially recorded PEFR and FEV1 records that reflects both variation in the non-asthmatic components of airway irritability and variation in the patient's tolerance of the discomfort of a maximal respiratory effort because of tiredness or other factors. The physician remotely interpreting self-collected data, particularly if it includes with and without exposure comparison data on which to base a presumptive diagnosis of asthma, may be better able to recognize and account for this phenomenon if he or she has access to graphic displays of complete breath patterns.

For these reasons, some embodiments of enhanced electronic peak flow meter may have the configuration option to record complete breath data for all breaths performed in the course of measurements using a compare function provided as part of the present invention (i.e., not just the single breath chosen as "best"). In the alternative, breath tests may be done for designated periods of time in embodiments of the device with sufficient memory, to record complete breath data for all breaths recorded by the device by that individual, even if they are disqualified from analysis because of failure to meet the ATS specification for technical adequacy when the device is configured to require compliance with the ATS standard for inclusion in the selected data set.

A preferred reporting option for this function in backup software will allow the screen display and/or printing of from 4 to 12 appropriately sized graphic images per page of the flow-volume curves of these respiratory efforts, sorted in order of decreasing FEV1 or decreasing PEFR.

The irritant changes in respiratory flow pattern in this condition are usually more marked in the inspiratory half of the flow-volume curve, which is not recorded by unidirectional flow measuring devices designed to measure PEFT and/or FEV1. Devices using bidirectional sensors with sufficient precision and accuracy in both directions can be adapted to record inspiratory as well as expiratory airflow, and devices to measure bidirectional airflow can be constructed using unidirectional flow sensors with the use of paired sensors, one to measure airflow in each direction. The design and use of such devices was discussed in an earlier section of this document.

The complete forced respiratory maneuver needed for tracking of the full flow-volume loop can be performed either from maximal inspiration as a maximal forced breath out until all air is exhausted from the chest followed by a forced inspiration to maximal inspiratory capacity, or in reverse order from empty chest to empty chest. In asthma it is usually performed by blowing out before breathing in; so that if the patient happens to cough and interrupt the procedure in midstream, the expiratory flow parameters used to track asthma activity will already have been recorded. In office settings this maneuver is typically performed with staff supervision and coaching ("blow, blow, blow; suck in, suck in, suck in") to assure a maximal effort and this is not a procedure most patients can be expected to do reliably at home, twice every day for ever. Most adults can probably do it reliably for two weeks, however, and possibly repeat the effort at intervals of 6 to 24 months, if advised that this short term effort will aid in their diagnosis and management.

The devices needed to record complete flow-volume tracings may be different devices than those needed for the convenient and cost-effective monitoring of PEFR and FEV1. For this reason it is desirable to have software-compatible embodiments of the device for which the entire device can be effectively disinfected and all parts subject to contamination with respiratory secretions can be thermally and/or chemically sterilized. For patients for whom this irritant phenomenon is suspected as a confounding factor in the evaluation or management of their asthma, their management can be optimized if they can be given a device of this type to take and use for two weeks, with instructions to blow at least two maximal flow-volume loops twice each day in the course of their routine pulmonary function monitoring for this period of time.

Invention feature of incorporation of prompts, additional data recording and correction options for assignment of "circumstances of testing."

For unenhanced electronic peak flow meters for which the alert notification threshold is a numeric value for each of FEV1 and PEFR selected by the treating physician, there is no effect on subsequent meter operation if the patient's baby brother finds the meter and blows into it, if another family member with asthma borrows it to check his or her own pulmonary function, if the patient makes a game of seeing if he or she can make the display achieve different numbers, or if readings are taken without accurate specification of circumstance. The enhanced electronic peak flow meter gives a much more precise measure of asthma activity, If a non-serious blow triggers a warning alert message, it just isn't taken seriously.

The more precise and sensitive tracking of asthma control achievable by statistical process control analysis, however, will be confounded by the inclusion of erroneous or incorrectly classified measurements.

This is the reason for the presumptive classification of meter readings as routine AM or routine PM readings based on time relationship to the entered usual waking time, and prompting of the user to either accept these classifications, amend them, or supplement them by the addition of other classification categories. Similarly, a reading classified as for comparison can be presumptively classified as post-exposure symptomatic if there is no unmatched post-exposure comparison record in memory, recorded by that user within the prior 7 days. If there is an unmatched post-exposure comparison record less than 7 days old in memory for that user, the presumptive classification when the user designates that the test to be recorded will be a comparison reading, will be a without exposure reading to match with the most recent unmatched post-exposure test in memory. In either case, the user will have the opportunity to either accept or change any parameter of the presumptive classification. Comparison readings may be stored either with or without being matched at the time, and may be matched with other readings even if they were not originally designated as comparison measurements (though in that case a complete electronic breath record may only be available for the "best" breath and not for all breaths recorded in the course of that test). Thus, for example, a user who becomes symptomatic on going outside to shovel snow from his driveway in the morning could take a "symptomatic post exposure" reading and compare it with the routine AM reading he took an hour earlier. A high school student who coughs one day during gym could take a "symptomatic post-exposure" reading at the time, compare it with a "without exposure" reading taken at the same time the next day, and then, if he feels well enough to go to gym again, compare the same "without exposure" reading with a "post-exposure" reading taken an hour later. If he has respiratory symptoms again and decides to use an asthma rescue inhaler, he can record yet another reading "post rescue inhaler" for comparison with both the "without exposure" and "symptomatic post exposure" test results If a patient records an incomplete AM reading, for example only two breaths when the standard for either PEFR or FEV1 as the primary output variable specifies a minimum of three breaths) and then another breath, 10 minutes later, the most likely scenario, which may be presumptively assigned as a default for the user to confirm or correct, would be that the patient was symptomatic at the time of the first two breaths, too short of breath to complete the test, and that the third breath 10 minutes later represents a value after using a rescue medication. An alternate scenario would be that the phone rang, and that the patient recorded the third breath to complete the test after finishing the phone call. Default test assignment prompt algorithms may be composed for a variety of common scenarios. Some embodiments of this feature may remember user responses to default circumstance assignment prompts, so that if a patient has designated a third breath 10 minutes after completing two breaths of a breath test as completion of the previously started test on at least two of the most recent 3 circumstances on which this event occurred, he or she will then receive a "confirm or correct" prompt identifying this circumstance as "completion of test started xx number of minutes ago" as long as this continues to be the dominant response.

A major economic benefit of appropriate peak flow meter use is its allowing safe reduction, when tolerated, in the use of costly medications. While statistical process control analysis of pulmonary function data provides a much finer level of feedback monitoring of asthma control than simple visual review of unenhanced peak flow meter data, additional enhanced data input and tracking functions can make it easier to achieve more accurate tracking of the user's asthma, need for treatment and response to treatment over time.

Many paper peak flow meter record forms have columns for patients to record daily use of both controller and rescue medications, making it possible, if this data is recorded, to track disease activity and need for rescue medications as functions of controller medication dose. Unfortunately, in the real world, patients are often too busy to record the requested information, especially when they're feeling well. The enhancements of the present invention include several options to facilitate the collection of this data. Some embodiments of this invention may offer one or another, some may offer all as device configuration options.

For patients who treat their enhanced electronic peak flow meter as their constant companion and asthma personal data assistant, the most convenient way to record daily medication use may be to provide a data register in which each relevant drug is listed, with a counter to indicate the date, time and number of units (such as puffs) taken each time the medication is used. Others may find it more convenient to simply enter the number of units of each drug taken since the last routine AM or PM reading, with the default prompt at each routine AM or PM reading being the dose or number of units of each controller or preventer medication recorded for that time interval in the most recent prior entry. (A preventer medication is a rescue medication taken preventively before an activity that otherwise provokes symptoms. The most common preventive medication use in asthma is the use of an adrenergic rescue inhaler before sports or other active aerobic exercise.) Because medication use and particularly preventer medication use is often based on schedules of activities on specific days of the week, some embodiments of this feature may be configured to display default prompts to confirm or change reports of medication use based on recorded entries for the same AM or PM time span 7 days earlier. For well controlled asthma, which it is hoped will exist in almost all users of enhanced electronic peak flow meters as a result of the improved disease management made possible with these devices, non-preventer need for rescue medications will normally be less than one dose per day. For this reason, the default prompt to record rescue medication use should ideally be zero. There may be patients, however, for whom a more pragmatic choice would be the integer closest to the average daily, AM or PM number of doses or puffs taken during the past 7 days. (A dose of an adrenergic rescue inhaler usually consists of one or two puffs.) When patients skip a routine AM or PM reading, the medication use prompt might change to asking the patient to confirm or correct a daily drug use entry equal to the total daily use predicted according to the forgoing rules for the time interval since the last data entry.

The above data entry features are designed to make it easy for users to accurately record drug use in the most common circumstance, which it is expected to be when it's the same as it was a week earlier. Just as patients may be too busy to write down medication use when asked to keep manual records on paper, even if the interface for them to do so is designed to be quick and easy, they may be too busy to enter changes in medication use on their enhanced electronic peak flow meter. A preferred embodiment of this data entry function will prompt users to choose between accepting the default entry as accurate, correct it now, or correct it later. Users choosing to correct it later may be promoted by a soft beep in two hours, repeating every 5 minutes until the user either makes the correction or buys another two hours of silence by again electing to "correct it later."

Most real world device users will occasionally make data entry errors that they don't realize until after the fact. Enhanced electronic peak flow meters must therefore allow for retrospective correction of manually entered data, hopefully with user-friendly interfaces, The amount of configuration data needed for user-friendly operation, including text strings for medication and other display fields, will necessarily be cumbersome to enter directly into a device with a keyboard and display designed for compactness and economy in post-configuration operation. Preferred embodiments of the enhanced electronic peak flow meter will therefore have an interface that allows efficient configuration via a connection to a personal computer.

Invention feature of sharing data and analytic functions across a network:

It is believed that the most efficient and cost-effective way to screen for asthma or inadequately controlled asthma in school settings is to equip every sports coach, gym teacher, and every teacher who will supervise other active aerobic activities or play with an enhanced electronic peak flow meter, and train them to take a "symptomatic post exposure" reading and record the pulse rate for any child under their supervision who displays any of a list of signs or symptoms suggesting asthma. Children displaying any of the same symptoms in other school settings, in the absence of aerobic activity, can be sent to the nurse for testing. Children with symptoms associated with exercise can record "without exposure" comparison tests at about the same time on the next school day. Children who are symptomatic without exercise, often because of respiratory infections or peak allergy seasons, can have comparison testing to document the difference in pulmonary function and respiratory flow pattern when they get well or after receiving treatment. The logistic efficiency of allowing children to record their symptomatic reading on one meter in one setting and their "without exposure" comparison reading on another meter and the need for documentation of findings make it desirable to offer either a version or a configuration of the enhanced electronic peak flow meter able to share data and analytic functions across a network.

In a preferred embodiment of this feature of the invention, demographic data for each student including name, student record ID number, date of birth, height, and gender will be loaded into backup software. One embodiment of enhanced electronic peak flow meter designed to accommodate this feature will have a small numeric keypad to allow entry of the student ID number, and an interface to easily enter the circumstances of that reading, including the sport or activity associated with the symptoms, the signs and/or symptoms (as cough, shortness of breath, etc.), whether the student admits to or was observed to have signs or symptoms of respiratory disease prior to the sport or activity, and whether the student forgot to take a prescribed medication prior to the precipitating sport or activity.

In a preferred embodiment of this feature, data will be downloaded from the meter with which the student was tested to the network, and either complete data for that student transferred to the nurse's enhanced electronic peak flow meter or made available on a terminal in the nurse's office with a network configuration allowing immediate transfer of the follow-up reading to be transferred from the nurse's enhanced electronic peak flow meter to the network. The backup software for school or other institutional network use will include prediction algorithms for PEFR, FEV1 and any other pulmonary functions being measured. Upon completing the follow-up "symptom-free" or "without exposure" reading, the nurse will be able to display, print out, and/or fax or electronically transmit to the student's physician, a record including without symptom usually asymptomatic and symptomatic post exposure readings, each PEFR and FEV1 measurement as a percent of predicted, the change in FEV1 and PEFR associated with exposure, and print-outs of all relevant flow-volume and volume-time tracings. If the student has a history of prior use of the system, those records can be pulled, printed, faxed or transmitted at the same time.

Enhanced electronic peak flow meters equipped or configured for the network data sharing feature will also be able to accommodate "guest" users whose background information is not pre-loaded in backup software.

While it is expected that the network data-sharing feature of this invention of greatest value to schools and other institutions will be the ease and efficiency with which it permits the presumptive inclusion and exclusion of the diagnosis of exercise-induced or exercise-exacerbated asthma, it is likely that in some schools and institutional settings, networked data-sharing of the statistical process control function may also be of value. In schools serving socio-economically disadvantaged populations in which home management of asthma is often deficient, school-based statistical process control analysis of PEFR and FEV1 measured at the beginning (routine AM equivalent) and end of each school day (routine PM equivalent) will give the school nurse a highly precise real time view of the asthma activity of patients selected for this tracking, and the opportunity to initiate early intervention in those patient populations in which the lack of timely intervention all too often results in avoidable morbidity, use of costly hospital-based resources, disruption of the child's school and educational experiences, and occasional mortality.

The same data transfer feature can let a user who borrows someone else's meter or uses a shared meter at school, download and transfer his data to both his own set of backup software and his own identical or compatible enhanced electronic peak flow meter Specialized embodiments of the enhanced electronic peak flow meter of this invention may be developed to facilitate network use in schools or other settings in which almost all users will have unique file or identification numbers. Such embodiments might have numeric or alphanumeric keypads for the recall of these numbers or a base connected to a computer from which demographic data and prior records of the individual being tested can be transferred either before or after his or her test has been started. Other specialized embodiments may be developed, as was discussed in a previous section of this document for short term use by patients for whom recording of complete maximal respiratory flow patterns (inspiratory as well as expiratory phase) is desired.

One purpose of this invention is to facilitate the accurate and efficient collection, analysis and presentation for health care management decision-making of various clinically useful forms of respiratory data. The invention comprises a class of networked devices designed to perform a set of tasks, every one of which could be performed with pre-existing devices, methods of analysis and modalities of presentation. The invention proposes solutions to problems of inefficiency and inconvenience with pre-existing methods throughout the chain from data collection to impact on patient care, problems of possible transcription inaccuracy in delivery of data the point of analysis and of integration of results with other aspects of patient disease management, and problems of timeliness in translating the results of testing into improvements in patient care.

While it is anticipated that components of the technology associated with this invention will be licensed among competing device manufacturers, one goal of the invention is to facilitate the efficient collection, analysis and presentation of clinical data for health care management decision-making, and, if necessary, the establishment of standards to make these devices compatible with software and data storage formats that will allow the universal sharing of data, including the ability to transfer data back and forth between different manufacturers' back-up software and possibly also between devices of different manufacturers. This may be facilitated through the use of open source code for the database and data analysis software. It may require conversion between data collected from each of the two methods of flow measurement (measurement of flow with electronic integration to derive volume and measurement of volume with electronic differentiation to derive flow). It may also require data registers for the naming and matching of classification codes, for which the format and default classification options should therefore be standardized for different enhanced electronic peak flow meters.

It would be useful if each data item could be identified, when this data is available, by the device with which it was collected or the outside source from it came, if that device is able to accommodate that pulmonary function parameter.

The proposed universal electronic peak flow meter database format should be able to accommodate all conceivable forms of pulmonary function data, so that it may be used for the concurrent display of home electronic peak flow meter data, statistical process control charts and scores based on this data, office spirometry, clinical pulmonary laboratory data, arterial blood gas data, pulse oximeter readings, in a flexible variety of display formats.

Invention feature of automated long term tracking for accelerated loss of pulmonary function in backup software.

This feature of the invention will be implemented in backup software rather than directly in the enhanced electronic peak flow meter. It is considered novel as an automated application to improve the identification, long term control and hopefully long term outcome of a high risk subset of asthmatics, and it is only the other features of this invention that make this feature practical.

This is because prior to the availability of the semi-automated statistical process control analysis feature of this invention there was never enough of a motivation for patients to use home peak flow meters with sufficient regularity, when feeling well, to make it practical to track home-measured pulmonary function parameters for accelerated rate of decline. If the meter only alerted you to implement the next step of an asthma management plan when your PEFR or FEV1 fell below a pre-set threshold, and you knew that when you were feeling well and weren't getting a cold you rarely fell below that threshold, why take the time and effort to blow into the meter when you were feeling well. On the other hand, semi-automated statistical process control analysis in the enhanced electronic peak flow meter being used every day provides a level of real time precision in the day-to-day assessment of disease activity in patients with all levels of persistent asthma that allows the safer reduction in intensity of treatment when disease activity decrease and provides a safer early warning when activity increases, than would otherwise be possible. Use of statistical process control analysis of appropriately spaced daily home-measured parameters of pulmonary function is to asthma as use of appropriately spaced daily home monitoring of blood sugar level in diabetes: It provides an otherwise unavailable margin of safety for the reduction in medication use when disease activity decreases and earlier and more precise guidance to increase medication when disease activity increases than would otherwise be possible. The outcomes are better disease control with reduced total use of medications, reduced total cost of medications, and reduced adverse side effects of treatment.

The various parameters of pulmonary function normally increase with growth during childhood, and decrease with advancing age as our bodies wear out. The mean rate of loss of lung function with increasing age is greater in asthmatics than in healthy individuals without asthma. A small subset of asthmatics experience a much more rapid rate of decline, ultimately leading to premature respiratory failure. There is presently no "standard" treatment to retard these patients' accelerated loss of lung function, perhaps in part because prior to this invention there has not been an efficient method by which these patients can be identified early in their course. At this time these patients are usually identified when a treating physician, if he or she happens to record serial office pulmonary function results as percent of predicted value on a flow sheet or maintain a long term graphic record that can be easily scanned in the course of an office visit, happens to notice that key pulmonary function parameters charted as percent of predicted value have slowly fallen by about 50% over a period of about 10 years.

Many such patients are never recognized until they experience end stage respiratory failure, because their physician focuses his or her attention on treating the symptoms of the day and never adds to the time demands of follow-up care by tracking long term trends in pulmonary function. Many computer-based office spirometry programs track trends in various pulmonary function parameters, but these programs usually display results over periods of months rather than years. Furthermore, most asthma patients tend to have more office spirograms during exacerbations than when well, introducing a variable downward scatter into plots of trends intended to represent chronic change. This, and the fact that office well care measurements are relatively infrequent, make office spirometry a relatively inefficient way to screen for early indications of accelerated pulmonary function loss.

The efficient and cost-effective early identification of asthmatics with accelerated loss of lung function, made possible for the first time with the present invention, offers a major benefit in public health. At the present time, patients with accelerated loss of lung function are typically not identified until their disease is advanced and unlikely to respond to treatment. Early identification of cohorts of patients with early stage disease would permit the systematic study of interventions while the accelerated rate of disease progression is more likely to be amenable to treatment.

PEFR is a relatively insensitive measure for accelerated loss of lung function, as it has too much scatter. FEV1 is a good measure of accelerated loss, as are FVC and its surrogate measure, FEV6, for which home measurement may in the future become practical. The data density that can be achieved with twice daily routine home measurement of FEV1 should be sufficient to generate statistically significant trending over periods of months, rather than years. One might expect trending of routine AM and PM measurements not flagged as associated with increased symptoms (i.e., "well" measurements) to be a more sensitive indicator of accelerated decline in baseline, best chronically achievable or "well" pulmonary function than trending of all routine AM and PM readings including those depressed in association with symptoms. It is possible, however, that for patients who are symptomatic much more often than not, there will be so few "well" data points that trending based on all routinely scheduled AM and PM readings becomes more sensitive. It will be easy in backup software, if data entries are appropriately classified as has been previously discussed, to perform trend analysis both ways and issue warning alerts based on either analysis. Standard statistical analysis can assign confidence limits to calculated extent of decline and rate of decline derived from cumulative actual measurements.

Observed rates of fall in FEV1 or other relevant pulmonary function parameters may be evaluated for accelerated loss in either or both of two ways. The first and simpler method is applicable to patients above the age of about 30. The second, for which the analytic procedure is more complex, is applicable to patients as young as age 5-6 years.

The first method is based on the generally accepted approximation of 1% per year as being the "normal" rate of decline in the absolute value of most pulmonary function parameters in individuals above age 30. Experience with the tracking of large cohorts of patients will determine reasonable cut points for the flagging of patients as potentially having accelerated loss of pulmonary function, which may (for example) turn out to be declines at a rate greater than 3% per year measured over a period of 15 months, a rate greater than 2% per year measured over a period of 27 months, or a rate greater than 1.5% per year measured over a period of 63 months, in each case with the secondary requirement that either the confidence interval around the calculated current rate of decline or the confidence interval around the calculated mean rate of decline exclude the normal value of 1% per year.

The second method is based on comparison with predicted normal values, for which prediction algorithms can be incorporated into the backup analytic software. Different sets of prediction equations have been validated for different age ranges, and sometimes for different ethnic populations. When patients are tracked across a gap between the coverage range of different prediction equations, gaps between the predicted values generated by an equation valid up to age 17 and one valid for age greater than 18 can be smoothed, for example, by calculating interpolated predicted values equal to the predicted value according to the equation validated through age 17 times a factor of 1 minus the fraction of the year between the $17^{th}$ and $18^{th}$ birthdays that has elapsed as of that date, plus the predicted value according to the equation validated from age 18 times a factor equal to the fraction of the year between the $17^{th}$ and $18^{th}$ birthdays that has already elapsed. This results in a linear shift from the younger predictive equation to the older one over the course of the year of the switch.

Some predictive equations have upper age limits and others lose their precision at elevated age, reflecting limited numbers of healthy elderly individuals in the populations from whose pulmonary function measurements they were derived. In most patients suffering from accelerated loss of lung function the diagnosis will be evident long before they reach the upper validated age limit for an adult predictive normal equation. When a patient being tracked under this feature of the invention does reach such a milepost, however, their predicted normal comparison values may be modulated to a prediction equation that remains valid for their new age range in the same manner described above for prediction equation shifts between childhood and adulthood. Alternatively, when an elderly patient reaches the upper validated age limit of an adult predicted normal equation, his or her predicted normal value may be calculated as the upper age limit value under that equation—1% per year for age above that limit.

The inventor of the present invention is an allergist with a 30 year interest in keeping severe and labile asthmatic out of hospitals and emergency departments, by methods including timely increases in treatment to balance the increases in disease activity that otherwise drive exacerbations requiring hospital and emergency department care. He is equally interested in the other side of the same coin, reducing the cost and side effects of over-treatment when the disease is less active and medications can be safely reduced. He has been an active proponent of peak flow meter use since the first generation of these devices appeared in the 1970's. He has long been an active proponent of their use in the anticipatory management of severe and labile asthma, as screening tools for the presence of asthma or the presence of inadequately controlled asthma in school sports and physical education programs and for cost-effective screening for asthma and other forms of increased airway irritability in adults with exercise-associated shortness of breath. He has been saddened as a clinication, however, to see that each new generation of peak flow meter technology, prior to the present invention, still failed the market acceptance test of readiness for prime time, as indicated by almost trivially small percent use by asthmatics who have had previous severe exacerbations or even multiple previous severe exacerbations, by schools that have significant problems with asthma in their student populations, and as an economical way to screen for respiratory factors in the evaluation of adults with exercise-associated shortness of breath, and as an efficient way to track asthma patients for early identification, hopefully in time for more effective intervention, for the subset of asthma patients with accelerated loss of lung function over time.

The barrier is not economic. The typical savings in medication costs that appropriate use of a meter can provide for the average patient with moderate persistent asthma, who is typically overtreated 95% of the time to reduce the frequency and severity of exacerbations, would more than pay for one of the most sophisticated present or proposed electronic peak flow meters every month, and pay for several more each time their use prevents an emergency department visit. However, the overwhelming majority of patients who could benefit from regular meter use don't perceive enough benefit from their regular use to justify the inefficiency of data analysis and information flow that encumbers present peak flow meter technology. Why don't patients take the time to user their peak flow meters? A long as the only feedback is that YES, the patient is above the alert threshold, when the patient already has a pretty good idea that that's the case before they blow, it may not be time worthy to perform the test and record the results even if a computer does most of the record-keeping.

Measurement of blood sugar in diabetes is an example, if one recognizes that lung function is normally more variable than blood sugar so that what is analogous to a single measurement of blood sugar at a known time after food, activity and insulin is not a single momentary measurement of PEFR or FEV1 but a comparison of the present range and variability of those measurements with past measurements under similar or comparable circumstances. Prior art peak flow meters, whether manual or electronic, don't analyze patterns, and it takes more time than most users are willing to spend to plot out values in different colors for AM and PM and make an eyeball estimate of "pretty much like it usually is" or "significantly different from the way it usually is." Furthermore, there are no standard ways to quantify this eyeball assessment of pattern difference, document it for efficient comparison with past and future patterns, and communicate it in a meaningful way to a treating physician. The feedback they give to the patient is like a blood glucose meter that only indicates readings inside or outside of the desired range, gives a value if outside, but doesn't give any information about level when within range. Just as with prior art peak flow meters, patients would use such meters when they have reason to suspect that they're out of range, but rarely bother to do so when they believe they're within range.

It is anticipated that with direct patient feedback about control of PEFR and FEV1 pattern, based on statistical process control analysis of readings taken under both routine and non-routine combinations of circumstances historically relevant to the asthma control of that individual patient and presented in a standard format that can be documented, transmitted to and discussed with treating physicians, enhanced electronic peak flow meters incorporating features of this invention will be perceived to be as useful in the management of asthma as electronic blood glucose meters are in the management of insulin-dependent diabetes.

In schools, appropriate use of peak flow meters in sports and physical education programs could dramatically increase the efficiency and reduce the cost of screening for asthma. Efficient asthma screening and monitoring in sports and physical education programs are the keys to effective asthma control in schools because sports participation is universal, exercise is a challenge capable of provoking symptoms not only in exercise-induced asthma but in inadequately controlled asthma regardless of its primary pathophysiology. Using each symptomatic student's normal sports and physical education activities as the test setting for his or her suspected asthma, with the information management features of the present invention, has the following advantages in comparison to presently popular school asthma screening programs: It enables testing that's directly relevant to the student's symptoms as it uses the student's actual symptomatic episode as the post-exposure measurement for testing, It is safe, as if the episode was severe the test can be completed without re-exposing the student to the episode associated with his or her symptoms, by obtaining the comparison "without exposure" reading on the next available school day under circumstances that are as similar as possible but without the precipitating challenge (which will usually be a sport or exercise). Because it only involves testing student who develop symptoms suspicious or asthma and only when needed to evaluate and follow-up their symptoms, it does not require the logistics and staff support of programs involving mass exercise challenge asthma screening. Because it does not expose students to any diagnostic challenges above and beyond their regular school activities, it does not require parental consent or medical monitoring.

Nonetheless, this type of school asthma screening is almost never done with electronic peak flow meters incorporating, and for the same reasons those meters aren't widely used by patients: Inefficiencies in information flow and data analysis with prior art peak flow meters make it more trouble than it's worth to exploit the benefits of a technology that if made more efficient could save schools with asthma problems many times their cost. School health officials would like to have the information that could be obtained from appropriate peak flow meter use, but they can't afford to allocate the resources and train the infrastructure of personnel needed to reliably perform with prior art technology what is automated in the present invention.

It is believed that enhanced electronic peak flow meters incorporating the compare and networking features of this invention should make it practical for schools to implement truly effective and efficient screening for unrecognized and/or inadequately controlled asthma that is more effective than any practically available alternative, more efficient in its use of school resources than any practically available alternative, and available whenever and wherever a suspect incident occurs although focused on sports and physical education programs as the areas of greatest clinical need and greatest diagnostic yield.

Electronic peak flow meters that also measure FEV1, if used regularly for sufficient periods of time, could facilitate the early identification of the subset of asthmatics with accelerated loss of lung function, when their disease will hopefully be more responsive to intervention. Long term tracking of FEV1 in backup software would not of itself require the enhanced electronic peak flow meters of the present invention, but it has never previously been practical as it requires a density of data when users are "well" (i.e., frequency of readings over time when not experiencing acute exacerbations) that is uncommon in users of peak flow meters that do not incorporate the statistical process control feature of the present invention. For this reason, the automation of long term tracking of FEV1 for the identification of patients with accelerated loss of pulmonary function has never been previously proposed as a benefit of peak flow meter use. As the increased use expected for meters that give their users the benefit of day-to-day statistical process control tracking of their asthma is for the first time expected to generate the routine and routine-well data density needed for long term tracking for accelerated fall in FEV1, this tracking is incorporated as a feature of the present invention.

In published longitudinal studies of FEV1 or its sometimes used surrogate measure FEF0.75 that use the same measuring technique over time, mean rates of loss of FEV1 in healthy individuals above age 25 are generally less than 30 ml./year. While experience derived from use should enable the selection of more efficient alert threshold levels, it is presently proposed that alerts be generated when the slope of a linear regression plot of well AM or well PM FEV1 (well meaning no other test circumstance flagged) is statistically greater than 40 ml./year over a tracking period of at least 15 months (to minimize risk of confounding by seasonal factors). It is proposed that the software also track the slope of linear regression plots of all AM and all PM FEV1 (i.e., with or without the flagging of other circumstances of testing), to determine the relative diagnostic yield of the two search criteria.

Invention feature of tracking response to inhaled rescue medications.

Both percent FEV1 response to rescue use of an inhaled bronchodilator of the adrenalin family and percent FEV1 recovery (percent of drop from current mean FEV1 for that time of day recovered following bronchodilator) are variables which, if they occur and are recorded with sufficient frequently to permit statistical process control tracking (i.e., in asthmatics who use their rescue medications on a fairly frequent basis), may be subjected to clinically relevant statistical process control analysis. In an asthma patient with moderate or severe persistent asthma who uses a rescue inhaler several times per week on a chronic basis, loss of statistical process control for either percent FEV1 response or percent FEV1 recovery and particularly the concurrent loss of statistical process control of both of these variables are likely to be indicators of increasing asthma activity. Whether complex parameters such as these are earlier indicators than loss of statistical process control for routine AM and PM measurements or for the absolute numerical value of measurements taken either before or after use of a rescue bronchodilator, and, if so, for what types of patients, remain to be determined by experience after the devices become available.

Measurements taken to track response to a fast-acting rescue bronchodilator must be taken after a constant time interval following inhalation of the bronchodilator, if comparison or statistical process control analysis of the readings are to have any value. This can be standardized by choosing a constant time interval for each patient that reflect the time course of action of the drug used for rescue and the patient's willingness to wait to record post-bronchodilator FEV1. Each patient is his or her own control for these measurements, so it is less important to choose a time interval to measure peak drug effect than to choose a time interval with which the patient is more likely to comply. As patients sometimes use different rescue bronchodilators at different times, certain embodiments of this feature will have data registers to list the different rescue bronchodilators used by that patient and the time interval to wait to take a post-bronchodilator reading after each one. Preferred embodiments of this feature will be physician-configurable to list either a designated most commonly used rescue bronchodilator as the default selection (on occasions on which the patient tracks response to a different bronchodilator he or she will have to press some keys to choose a different medication, or to set the default selection to the whichever rescue bronchodilator was most recently used in the past. In a preferred embodiment of this feature of the invention, the time interval between dosing and post-bronchodilator will be displayed together with response data on physician backup software and it will be possible to display response as a function of time from dosing to measurement. The physician or other reviewer will have the option to select data subsets for separate analysis on the basis of parameters including range of time intervals between dosing and measurement of response.

Patients will be asked to push a button on their devices to indicate when they take rescue medications, to permit tracking of the time interval between dosing and post-bronchodilator testing for response, It is not intended that compare readings or readings taken following administration of rescue bronchodilator be mutually exclusive from readings taken for the purpose of statistical process control tracking if the compare readings are taken on a personal enhanced electronic peak flow meter used for statistical process control tracking by the same user. It is intended that the same reading taken for multiple purposes be able to be classified as such, so that the resulting data can be used for each analysis for which it qualifies.

Analyses based on PEFR, a less precise indicator of asthma activity than FEV1, will generally be more variable and less predictive of changes in asthma activity than similar analyses based on FEV1. Because changes in PEFR and FEV1 should be generally concordant in asthma and less so in airflow obstruction from other causes, many embodiments of enhanced electronic peak flow meters and backup software of this invention will track PEFR as well as FEV1, so that concordance or discordance between the two is apparent to those reviewing data.

Invention feature of flagging measurements taken following exposure to potential triggers or aggravators of asthma, for comparison with unexposed values (the comparison feature of this invention) measured either before exposure to the trigger or under pre-exposure circumstances on a different, usually subsequent day.

The questions of incriminating or ruling out asthma as a factor in exercise-associated respiratory symptoms and in respiratory symptoms associated with exposure to a broad range of potential allergens and respiratory irritants are often not addressed with a high degree of efficiency by technologies in existence prior to the present invention. Challenge tests for exercise-induced asthma in school settings are cumbersome and demanding of staff and/or volunteer time, require parental consent which is often not easy to obtain for those students for whom the question is most vexing, and may give false negative results if a student is tested under circumstances that do not totally reproduce those associated with symptoms (e.g., cold air temperature with close exposure to a moldy football or soccer field at a time when the patient may also have a cold). Testing for asthma as a factor in exercise-associated respiratory symptoms in adults requires a costly physician-monitored cardiopulmonary stress test, which may give false negative results for any of the reasons already listed for children or additionally because the gradual rates of exercise increment that are used to increase cardiac safety may desensitize physically fit subjects and thus fail to detect exercise-induced asthma. Testing for asthma as a factor in environmentally induced respiratory symptoms requires replication of those exposures in a medical study setting, which is often cumbersome, costly and may give inaccurate results because of failure to duplicate unrecognized critical features of the setting and circumstances of the original symptoms.

Present diagnostic technology typically attempts to replicate real life challenge exposures so that pulmonary function following exposure can be compared with that measured prior to exposure. There is no reason why unenhanced electronic peak flow meters could not be used to measure PEFR and FEV1 when symptoms are present following exercise or following an identifiable environmental exposure, and the post-exposure readings compared with "unexposed" readings taken at the same time (to eliminate diurnal variation as a confounding factor) on the following day or the following school day or business day. (An increasing time lapse between "exposed" and "unexposed" comparison measurements increases the risk of confounding by unrecognized factors, but the simplicity and economy of obtaining an after-the-fact "unexposed" reading to compare with a symptomatic "post-exposure" reading makes it extremely practical as a screening test despite these confounding risks.) However, as with the other enhancements comprising this invention, most people who could benefit from this data processing function either can't perform it reliably by hand or won't do so, and the remaining fraction who could and would is so small that it isn't effective for physicians to incorporate it into their disease management protocols, so that without the enhancement of this invention it just doesn't get done.

Conditions other than asthma can cause both exercise-associated respiratory congestion and exercise-associated drops in PEFR and FEV1 that mimics those caused by asthma. Pulmonary function patterns associated with these non-asthma mimickers of asthma may either meet or fail to meet the parameters of a technically adequate respiratory effort for measurement or FEV1. As the goal of this feature of this invention is to facilitate the accurate diagnosis of asthma by documentation of pulmonary function whenever and wherever symptoms occur, it will encompass the following features in various embodiments to facilitate this goal:

Unenhanced electronic peak flow meters typically extract numerical values for PEFR and FEV1 from electronic measurements of flow or volume recorded at a rate that is usually approximately 50 measurements per second for the duration of the breath. To conserve memory, they typically store only the extracted PEFR and FEV1 values and in some devices only store them if the breath pattern satisfies an embedded algorithm for technical adequacy for measurement of FEV1. The increased precision with which an asthma specialist physician can make a remote diagnosis of probable asthma will justify the increased investment, in the manufacture of some embodiments of enhanced electronic peak flow meters, of increased on-board memory or the capacity to accommodate the same types of removable compact memory chips used in digital cameras, to permit the storage of complete expiratory flow or volume data, for downloading and possibly for recall and display in the standard formats of flow vs. volume and volume vs. time on the screens of those embodiments of the invention.

It may be helpful for physicians reviewing statistical process control reports to view complete graphic displays of selected test breaths, to differentiate patterns characteristic of asthma from patterns suggesting conditions that might confound the diagnosis and/or evaluation of asthma. As the storage of complete breath data will compete for memory space with the ability of the enhanced electronic peak flow meter to store parameters derived from the analysis of complete breath data for longer periods of time, and enhanced electronic peak flow meters can be designed to accommodate supplemental memory cards of variable capacity, preferred embodiments of this feature of the invention will have configuration options to store complete breath data for "best" breath (the one selected for storage and analysis) from each test, to store complete breath data for the best and worst test in each category (such as routine AM test) in each 7 day period, and not to store any complete breath data in order to conserve memory for the storage of derived pulmonary function parameters for more tests.

If one is making a remote diagnosis of probable exercise-induced asthma or probable asthma induced by exposure to some other potential trigger, it is reassuring to confirm that the baseline FEV1 and PEFR are each approximately percent of predicted normal value for an individual of that age, sex and height, and that the post-challenge FEV1 and PEFR are also approximately the same percent of the same predicted normal value. It would be possible to encode algorithms for the calculation of predicted normal values in flash memory in some embodiments of this invention, to provide this information. However, because this feature of the invention can be most efficiently implemented and documented if data is downloaded to the computer of the treating physician, it will probably be most efficient if the algorithms for calculation of predicted normal values are stored in backup software, either in addition to or instead of being stored directly on the enhanced peak flow meter.

Examination of both expiratory and inspiratory components of the flow-volume display of a maximal respiratory effort is the best way to rule out an irritant process that could lead to an incorrect diagnosis of asthma. Portable spirometers, devices capable of recording both expiratory and inspiratory flow, are not well suited for distribution to patients to take readings when they experience symptoms because they are generally more bulky, much more costly, much less rugged and easily damaged in rough handling, and many require calibration each time they are moved. Most electronic peak flow meters are only designed to record expiratory flow. For this feature of the present invention, selected embodiments of enhanced electronic peak flow meters using unidirectional flow metering technology can be designed with paired sensors to measure inspiratory and expiratory airflow. The same function can be performed with enhanced electronic peak flow meters using bidirectional flow metering technology by recording and storing inspiratory as well as expiratory flow measurements.

The performance of a maximal complete expiratory and inspiratory effort is a task we have previously described as unrealistically demanding for most patients to perform reliably without medical supervision, for the routine daily tracking of pulmonary function parameters for statistical process control analysis. It is not believed that the same consideration applies to the "compare to" feature of this invention. There is so much useful information to be obtained so much more efficiently than by any other means with this use, that it is expected that most patients (including some but not all young children), with proper instruction (and parental or school nurse coaching for children), to be able to perform the necessary maximal respiratory effort for the few breaths needed to perform the comparison function of this invention. Furthermore, professional coaching and supervision may be available in many test settings. Examples follow:

In individuals who are candidates for cardiac stress testing, respiratory disease, specifically asthma, is often an important differential diagnostic consideration. Both cardiac and pulmonary function measurements can be obtained in most hospital cardiopulmonary laboratories, but it is generally more efficient and cost-effective for cardiologists to perform the cardiac component of the test in their own offices, in which pulmonary function testing is generally not available. With enhanced electronic peak flow meters incorporating the compare feature of the present invention, the patient need only be given a properly equipped and configured enhanced electronic peak flow meter, taught how to perform a maximal expiratory/inspiratory flow maneuver, instructed to record three breaths before beginning the test, to record 1 to 3 breaths at the end of each step of the test, and to record three breaths between 8 and 15 minutes after completing the test. The device can be returned to the physician evaluating and/or treating the patient for respiratory disease, and one has the data yield of a simple cardiopulmonary stress test with the convenience of a cardiac only stress test.

An individual reporting occasional shortness of breath either with or after aerobic exercise may be given an enhanced electronic peak flow meter incorporating the compare feature of this invention, instructed in the proper respiratory maneuver for recording, and told to record three breaths the next time he or she experiences exercise-associated symptoms. He or she can record a comparison reading as close as possible to the next day at about the same time and in the same setting, giving the data yield of an exercise challenge test without the medical supervision that would be needed for a separate medical challenge and without the risk of yielding a false negative result because of not fully duplicating the conditions needed to provoke symptoms. Complex exposure circumstances may allow multiple possible comparisons. A measurement taken because of shortness of breath after running through moldy woods on a cold, wet day could be compared with readings taken the next day in the same woods under similar weather conditions but without running, readings taken after running in similar weather but not in the moldy woods, readings taken after a run through the same woods but in warmer weather, and readings taken when all factors are the same as when the patient experienced the symptoms but after taking a preventive medication before running. In general the original reading will be compared with a reading taken in the same location on the next day without running. Readings reflecting each of the other combinations of circumstances will generally be compared with readings taken in the same settings immediately before the patient runs.

With valved or filtered mouthpieces to prevent transmission of infectious organisms between users, this feature of the present invention would tremendously simplify the recognition of exercise-induced asthma and differential diagnosis of other causes of exercise-associated shortness of breath in school sports and physical education programs. This function can be made still more convenient and efficient with the data transfer and sharing feature of the invention, to be described farther down in the list of features encompassing the invention.

Feature of entry of pulse rate at the time of comparison readings associated with exercise: The full interpretation of exercise challenge tests for asthma requires documentation of heart rate both at rest (time of without-exercise comparison reading) and after exercise, and determination of the post-exercise heart rate as percent of predicted maximum according to the prediction equation, Max HR (pred)=220—age of patient. Almost any adult and almost any parent or other caretaker of children old enough to perform PEFR and/or FEV1 maneuvers should be able to count the number of pulse beats in 6 seconds and multiply by 10, or count the number of pulse beats in 5, 10 or 15 seconds. To facilitate the collection of this data, embodiments of the invention incorporating the compare feature may have fields to record measured heart rate or number of pulse beats and then the number of seconds in which these beats were counted. Personally used meters can be equipped with data registers to include the user's date of birth height and gender, and prompt for updated entry of height every 3 months for age less than 18 yrs and annually for age greater than 18. Height is relevant for the calculation of predicted values of PEFR and FEV1, which can be done in back-up software for meters not equipped to perform this calculation internally and uploaded to give the user the option to display his or her current results as percent of predicted. Calculated percent of predicted values displays can be programmed to blink to advise the user that they may be unreliable when the most recent height entry is older than 3 mos. or 12 mos. depending on age of patient. "Are you sure" prompts can be programmed to query height entries that do not have programmable age and/or sex-based relationships to that patient's most recent previous height entry. Guest registers on personally used meters configured for occasional or situational performance of the compare function by other persons can be equipped with registers for the same data for each user, with the option to enter age in years instead of exact date of birth for one time guest users although it is more reasonable to require date of birth if data is to be exported to the guest user's own device or back-up software. Height is irrelevant for guest users of meters not equipped for internal calculation of predicted normal values.

To facilitate both tracking of the epidemiology of asthma within schools or other institutions using the compare feature of this invention for asthma screening and monitoring and appropriate classification of circumstance for data to be exported to students' personal meters and back-up software, devices and device configurations optimized for school asthma screening and monitoring will include the option to flag data according to circumstance. Standard circumstance flags will be exported with the accompanying flow data. These include but are not limited to the presence of various respiratory symptoms, whether following exercise, exposure to cold air or both, suspected presence of a cold or other respiratory infection. Custom site-specific circumstance flags will not be exported as the data registers for user or site-defined flags will have different meanings in different users' records. An example of a site-specific circumstance in a school setting would be a meter reading taken following exposure to a classroom with a mold problem following a water leak.

Invention Application #2

Figure 5:
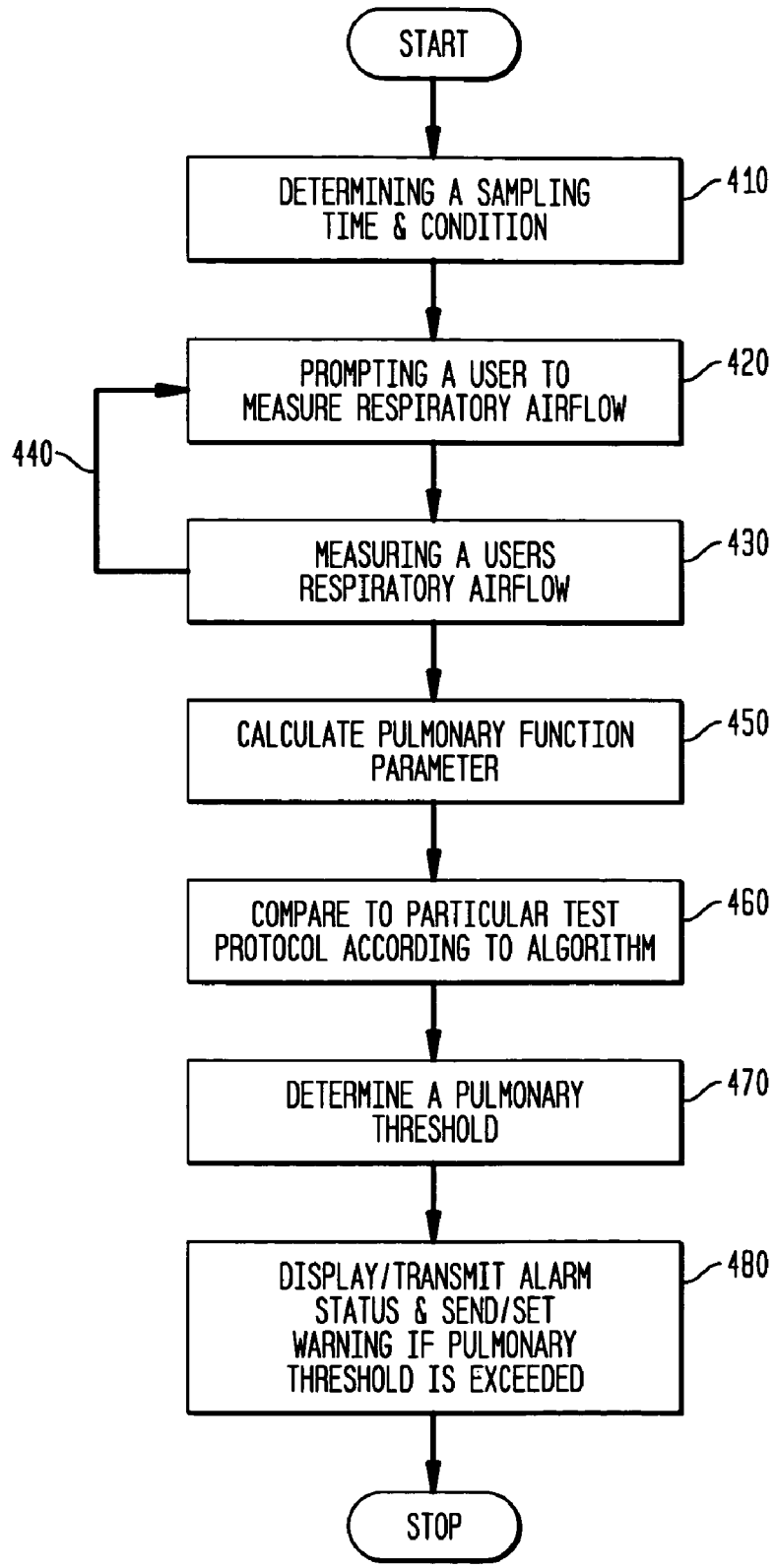
FIG. 5 is a flow diagram for taking respiratory measurements according to a second preferred embodiment of the present invention.

FIG. 5 provides another particularly preferred method according to which the statistical process control program is used to operate on the accompanying respiratory data. At step 410 a sampling time and potential trigger condition are selected and input into the EEPFM, potentially by using the key entry pad 16, such that a respiratory sample is scheduled to be taken either before or after a pulmonary stressing trigger event which is knows to affect the patient. Potential triggering conditions may include a past exposure time period immediately following an asthmatic trigger as provided below. Alternatively, this may be done automatically by the stochastic process control software after a degradation in respiratory performance noted by the software. At step 420 the patient is prompted by the EEPFM, possibly through an indication on the display 14, to take a respiratory measurement in response to the trigger. At step 430 the patient blows (or inhales) into opening 18 of EEPFM 10 and that forced respiration travels along pathway 20 to transducer 28. At this step the transducer 28 also converts the mechanical airflow into electronic signals which travel along bus 32 to electronics module 40. Also at step 430, the processor 45, possibly with the assistance of the processing circuitry 48 massages the data and stores it in data memory 50 for later processing by the statistical process control program. This portion of the process including the prompting of a user measurement of the respiratory airflow, measuring that airflow and conversion by the transducer and storage of the electronic values in memory may occur repeatedly according to repeat loop 440 and the need for repeated measurement as provided in detail below.

Following the storage of a statistically significant data set for respiratory measurements, at step 450 of FIG. 5 the statistical process control program held in stored program memory 55 operates on the data to calculate certain pulmonary function parameters. According to current medical practices regarding the treatment of asthma and other respiratory ailments, as discussed in detail below, a key pulmonary function parameter to be calculated is the peak expiratory flow rate (PEFR). This is the maximum rate of expiratory airflow achieved in the course of a maximal expiratory effort. Other more advanced expiratory flow rates, such as FEV1—the volume of air exhaled in the first second of a maximal expiratory effort—may also be calculated by the statistical flow program from the respiratory data within the data memory.

At step 460 the statistical process control variables are calculated by the processor 45, possibly in conjunction with the processing circuitry 48, according to the particular statistical process control program being executed. In particular, if PEFR is being measured and used to diagnose a patient's respiratory capacity, then a mean PEFR over a certain statistically significant period of time may be calculated for further analysis. If the pulmonary function parameter to be measured is FEV1, then the statistical process control variable may also be a mean FEV1 over a certain statistically significant period of time. Also at step 460, the pulmonary function parameters are compared to a particular test protocol according to an algorithm. The test protocol may be provided in software to detect a severity of degradation of pulmonary activity in response to the trigger. The algorithm may be a mathematical test operating according to the protocol.

At step 470 of FIG. 5, the statistical process control program calculates a pulmonary threshold associated with the appropriate statistical process control variable for a given pulmonary function parameter. Further, the pulmonary threshold may be conditioned by the pulmonary trigger test protocol. From a medical standpoint, as described in more detail below, this pulmonary threshold is likely to vary on a patient-by-patient basis, or possibly based on trigger type, given each patients particular medical circumstances as evaluated by the patient's physician. In certain statistical models, a first approach pulmonary threshold may be determined by the statistical process control software. This value may then be updated by the analysis of the statistical process in response to the respiratory data collected. In sum, the pulmonary threshold may vary over time or according to different environmental circumstances experienced by the patient or, for example, in response to a serious degradation of a patient's pulmonary capacity. As purely hypothetical examples of any particular patients' circumstances, a potential pulmonary threshold for PEFR may be set to be three standard deviations of the mean PEFR (the statistical process control variable). Likewise, a potential pulmonary threshold for FEV1 may be set to be 60% below the mean FEV1 (the statistical process control variable). Further, the test protocol and algorithm may look for significant deviations in the PEFR and or FEV1 such as a 10-15% over a particular testing period. In any case, however, the pulmonary threshold is a value that is associated with the statistical process control variable and pulmonary function parameter under the control of the statistical process control program. Whether determined a priori as a first choice of the statistical program control or whether subjectively set by the attendant physician based on an analysis of the patient's data, the pulmonary threshold indicates a trigger condition. As such, the process shown in FIG. 4 ends with an alarm display step 470 and possible transmission of the alarming condition the doctor's office indicating the alarm condition.

Particular test protocols and Algorithms according to a specific exposed response.

A second significant aspect of the present invention includes the use of the pulmonary function measuring devices to record responses to "anticipated and unanticipated" challenges without need for direct oversight by the evaluating physician. This feature involves the programming of the EEPFM to prompt, collect appropriately classified data and analyze the pulmonary function impact of a suspected asthma-triggering exposure with the simple step that no one else seems to have thought of, of collecting the "without exposure" comparison reading the day after the exposure suspected of aggravating asthma, instead of before the exposure. Ordinarily one measures the impact of an exposure, such as to exercise, by measuring the chosen parameter (FEV1 when practical, otherwise PEFR) before and after a challenge suspected of triggering or aggravating asthma, and calculating a percent fall in the measured parameter induced by the challenge. This is fine if one knows in advance which exposures that the patient will be undertaking anyway, in the course of his or her chosen pattern of activities, is likely to trigger or aggravate asthma. It becomes impractical if the triggering of the symptoms that after-the-fact suggest asthma is not anticipated ahead of time.

To test respiratory function after a suspected triggering event with the traditional approach, the patient must be brought back to the doctor's on another occasion, obtain a pre-challenge measurement, reproduce or attempt to reproduce the trigger suspected of provoking asthma symptoms, and measure the change in the chosen pulmonary function parameter. Sometimes it's impossible to adequately reproduce the challenge, giving negative test results whose significance becomes uncertain. More important, in terms of cost and burden on the health care system, when the patient undertakes the provoking challenge in the course of his or her chosen activity, the physician conducting the evaluation isn't responsible for any adverse effects that might result, and doesn't have to monitor or be prepared to medically intervene. If a physician wants to re-challenge a patient for the purpose of determining whether the replicated challenge provokes the suspected response and to measure the response in order to make or confirm a diagnosis, the physician becomes responsible for monitoring for potential adverse effects and must be prepared to intervene in the event of adverse consequence of the diagnostic challenge. For the confirmation of suspected exercise-induced asthma in school settings, this requires obtaining parental consent for re-challenge (which is often difficult in those underprivileged socioeconomic groups in which school asthma is a major problem). Further, the re-challenge requires physician supervision, which is cumbersome, costly, and if scheduled for a different time when the child has recovered from the viral respiratory infection that may have been an important factor in the initial reaction, the result may be negative because of failure to adequately replicate the challenge. If the patient is an adult, re-challenge requires cardiac monitoring and the immediate availability of cardiac resuscitation by trained personnel, at a cost of approximately $700 per challenge in addition to the cost of the pulmonary component of the test. As in the school example, scheduled re-challenge when all of the original factors may not be adequately replicated may give a false negative result. If instead of obtaining a pre-challenge measurement, one comes back at the same time the following day (or the following school day) to obtain a "without challenge" comparison reading, there will be a slight loss of precision in comparison to a reading taken before the challenge that provoked the symptoms. This loss of precision is less than the loss of precision caused by failure to fully replicate the challenge conditions in a subsequent diagnostic challenge, and the cost savings achievable by not having to bring patients back for separate diagnostic challenges with all the medical monitoring and (in the case of schools) requirement for parental consent for a challenge that might theoretically place the subject at risk This second invention application feature has three separate aspects. The first aspect is for the regular meter user, for whom it can help tell what's happening when the patient experiences respiratory symptoms in association with various exposures. If a patient with difficult asthma seems to finally be coming under good control, but experiences shortness of breath with sports or exercise, this use of his or her enhanced electronic peak flow meter should provide data to enable a treating asthma specialist to determine whether the patient is experiencing an exercise-associated exacerbation of asthma as indicated by a significant and ideally similar fall in both FEV1 and PEFR in the presence of other aggravating factors may also be at play, e.g. cold air, respiratory infections, prevailing allergens, etc. (there is debate in the medical community about whether a significant fall should be 10%, 12.5% or 15% and whether the same threshold of significance should apply to both PEFR and FEV1 and for which the appropriate patient management is usually to increase medications, or if the patient is simply out of shape, a graded program of physical conditioning. If a known asthmatic who is a regular meter user experiences acute coughing and choking after accidental or unavoidable contact with high levels of passive cigarette smoke, a significant and parallel fall in PEFR and FEV1 would suggest an acute exacerbation of asthma requiring an appropriate increase in medications. The absence of a significant fall in PEFR or FEV1 would suggest a non-asthma upper airway irritant reaction, for which appropriate management would be to get away from the smoke, drink and gargle warm liquids, and take a mild or moderate potency cough suppressant, and look for other potential contributing factors such as acid reflux.

The second aspect is for identification of either unrecognized or inadequately controlled asthma in schools, particularly schools with large socio-economically disadvantaged populations. Asthma is the most common medical cause of school absenteeism and a major barrier to school achievement. News reports abound about the occasional promising student athlete or other young celebrity who dies of an acute severe unrecognized exacerbation of asthma. One would be surprised by the inefficiency and ineffectiveness of school asthma identification programs throughout the country, and the amount of money consumed because of public health mandates to fund asthma screening without the people in charge having much of an idea of how to correct it.

Medical studies have shown in discussions with officials in school districts that major student asthma problems adduced with older, mechanical peak flow meters, may also use manual implementation of the same principle that is automated as a feature of this invention.

All kids without medical excuses take gym or participate in sports, which then becomes an added asthma trigger for susceptible students on top of whatever aggravating factors are at play. Thus sports and physical education become the venue in which the trigger of exercise is superimposed on top of whatever other asthmagenic factors are at work, making screening for low post-exercise PEFR or FEV1 with measurement of the "without challenge" comparison value at the same time on the next school day, the most efficient way to screen for asthma in school populations whenever and wherever it happens.

In both of the previous studies with school districts, manufacturers of the then-available mechanical peak flow meters were willing to donate the meters. One of these districts, at the time, was experiencing one ambulance call per month for acute severe asthma, usually triggered by physical education or sports. Yet neither school was willing to accept the gift of meters and disposable mouthpieces and free staff training in their use, for the reason of being unable to provide staff to do the necessary record keeping and clerical work when recordkeeping would be 100% manual. With most schools now having computer networks, the proposed network programming of this function makes it practical with initial software setup reading from the same student lists the schools already maintain, and total elimination of the data transfer functions that schools couldn't staff with older peak flow meter technology.

The third aspect of this feature of the invention is represented by a device furnished by the asthma specialist to a patient reporting exercise-associated symptoms in a setting that would be hard to replicate exactly in an allergy, pulmonary or cardiopulmonary office or laboratory. An example would be a patient employed as a casino security guard with the job of riding a mountain bike up and down the casino's customer parking ramp all day long, to look for trouble and to be visible as an incentive to customers not to cause trouble. This patient's problem was shortness of breath while biking uphill in the parking garage, but not all the time and not in association with any other identifiable aggravating factor, circumstance or trigger. He had a normal cardiopulmonary stress test, and it was never clear whether trials of various asthma medicines gave him any relief because of spontaneous variability in the occurrence of his symptoms.

This is a person to whom it would be nice to be able to give a device, programmed to let him indicate whether a reading was taken before he started to bicycle up the ramp or after cycling up, and also either whether he was short of breath or to indicate the severity of his shortness of breath on a scale of "0" (for none) to "5" (for severe). He could be asked to perform three 2-second maximal forced expiratory maneuvers before and at the top of each trip for a week, to note shortness of breath when present, and to bring the meter back or upload its data via phone or internet so that it could be displayed and reviewed in time for his follow-up visit.

Another bell and whistle feature that would facilitate the implementation of this feature of the invention is described below. This is the ability to record or enter heart rate for correlation with such other factors as symptoms and falls in FEV1 or PEFR. An association between heart rate at the top of a ride and the occurrence of shortness of breath could help explain this patient's symptoms and define his medical problem, for example. Options (embodiments) for heart rate entry include a button a patient could push at the pulse beat at which he starts counting, and pushes again at the 10th pulse beat thereafter. Other options could include coupling to a wrist or finger sensor of the type used in electronic home blood pressure monitors.

The first aspect will use the same meter that performs statistical process control analysis. The second may use the same kind of device or in a different embodiment or a different device specifically designed to interface with school or institutional network installations. The third, intended for repeated medically unsupervised use by one patient and then to be returned for use by other patients, must be designed in such a way as to permit disinfection of all parts capable of transmitting such agents as HIV, tuberculosis and hepatitis C virus from one user to another. This could be accomplished in a device using the flow sensor of Larom or paired sensors of the same type to measure both expiratory and inspiratory flow, by designing the head (FIG. 3 of that patent) to tolerate boiling, autoclaving, immersion for 30 minutes in 10% household bleach either before or after dishwasher washing, and office sterilization with glutaraldehyde.

Invention Application #3

This is an operating mode (if the same device) or a separate device designed to be given by the asthma specialist to a patient scheduled for cardiac stress testing, to permit easy and accurate collection of the respiratory data needed to perform a simple cardiopulmonary stress test. This cardiac portion is typically performed in the office of a cardiac specialist who typically knows little and cares even less about respiratory disease.

The most error-proof way to collect this data may be for the respiratory specialist or his or her staff to review the respiratory portion of the test protocol with the patient prior to the test, and then give the patient an enhanced electronic peak flow meter pre-programmed to prompt for and accept the test data in the proper sequence, together with a small PDA with a keyboard, programmed to accept answers to the questions on the spreadsheet figure on which the needed pulmonary data is listed in the Appendix.

This section is background information about the interpersonal dynamics of the setting in which this feature of the invention will be used and the ego trip barriers it must overcome in order to work. Cardiologists as a group tend to disregard other physicians' concerns compared to their saving of the patient's life, and they often will not take measures to assure that other doctor's vital data doesn't get entirely lost. The respiratory component of this test is thus most likely to get done with minimum ignoring of parts that are important to the allergist or pulmonologist but not to the cardiologist. If the patient is given a simple sheet with large print instructions to take to the cardiology lab, if baseline height and weight have been entered at the respiratory specialty office so this test data aren't lost if the cardiology office fails to enter them, but programmed such that the fields for their entry on the PDA at the cardiology office don't overwrite the values previously entered at the allergy or pulmonologist's office then the data for both physicians will be preserved. Saving both sets of values will give the respiratory specialist a clue if there was sufficiently gross neglect of their priorities that even basic height and weight data was entered incorrectly.

The pre-stress test data record on the spread sheet in the Appendix must be reviewed with the patient in the office of the allergist or pulmonologist. The instruction sheet for the cardiology lab must specify that the patient should complete the questions on the PDA and ask the cardiology staff to please assist the patient if he or she needs help. It should stress that the patient must take baseline FEV1 and PEFR readings for which prompts are pre-programmed into the enhanced electronic peak flow meter, before beginning the stress test. There should be data fields for "backup" readings taken in the allergy or pulmonary office when the patient was oriented to the respiratory part of the stress test procedure. This is to accommodate the situation in which the cardiology lab staff "happens" to neglect to let the patient take baseline measurements of FEV1 and PEFR, these surrogate "without challenge" values will be available so the espiratory component of the test will not be completely lost.

The cardiac laboratory staff should have simple instructions to push a button on the enhanced electronic peak flow meter as soon as the exercise is completed, to start the clock for the set of prompts programmed into the enhanced electronic peak flow meter for beeps and on-screen messages at the specified intervals at which the patient should blow into the meter for the measurements specified on the flow sheet. The patient should also have been instructed that this has to be done. At each time interval (after completing the needed breaths) the enhanced electronic peak flow meter should prompt the patient to record if any respiratory symptoms are present, offer a list of common symptoms (shortness of breath, cough, wheeze, tight chest) and also allow selection of "Other respiratory symptom #1" and "Other respiratory symptom #2", which, if chosen, should give a message for the patient to describe what these symptoms are in fields provided for this purpose on the PDA.

Cardiology staff will frequently forget to push the "exercise finished" button on the enhanced electronic peak flow meter and may forget to give the device to the patient in time for the first (5 minute) post-exercise reading. If the need for post exercise respiratory measurements has been stressed to the patient during orientation in the respiratory specialist's office, the patient is likely to remember at some time during the first 10 minutes after completion of exercise that these measurements should be taken. The enhanced electronic peak flow meter screen for entry of the "exercise finished" signal to start timing for reminders to record breath measurements should thus have an option to enter any estimated time lapse between the end of the exercise challenge and the time that the button was pushed.

At any time that FEV1 drops from baseline by more than 20%, the enhanced electronic peak flow meter should give both on-screen and audible prompts to take 2 puffs of albuterol or alternate rescue inhaler if symptoms are present, or repeat the reading in 5 minutes if symptoms are absent. If rescue inhaler recommended, the patient should be prompted to enter a time stamp when it is used and also the number of puffs taken. The device should then default to the schedule for follow-up of rescue inhaler use, as noted near the bottom of my spread-sheet illustration. If FEV1 has dropped by 20% or more and drops further following rescue inhaler use or has not risen to within 10% of baseline by the end of the 60 minute post-bronchodilator follow-up, the enhanced electronic flow meter should display a warning message to call the respiratory specialist, and it can be programmed to include his or her name and contact phone number.

Invention feature of tracking PEFR and FEV1 during cardiac stress testing for the efficient and economical addition of a pulmonary component to cardiac stress testing.

For physician convenience and economy, most cardiac stress tests in the U.S. are performed in cardiac testing laboratories in the offices of cardiac specialist physicians. These heart specialists are typically exclusively not equipped to perform concurrent testing for respiratory contributing factors or alternate potential causes of these patients' exercise-associated chest symptoms, and their specialty does not encompass the training or qualification to interpret pulmonary function tests. With electronic peak flow meters able to record FEV1 as well as PEFR it would be possible to train staff to coach patients in the performance of the PEFR and FEV1 maneuvers and record and document the necessary measurements to permit interpretation by physicians qualified to do so who do not have to be on site at the time of testing. As with the other applications discussed in this section, however, there are presently no standard protocols for the timing and extent of pulmonary testing as an appropriate screening or diagnostic adjunct to a cardiac stress test, Appropriate use of electronic peak flow meters incorporating features of this invention could add a simple pulmonary screening component to every cardiac stress test in almost any setting for essentially no cost beyond that of a disposable filter mouthpiece and the amortized one time cost of the device and backup software, for patients with a negative history for respiratory disease and a normal computer interpretation of their pulmonary screening results. For patients with a history suggestive of respiratory disease as a contributory or differential cause of shortness of breath with exercise, and for patients with a negative history but abnormal computer screening results, properly classified data recorded at the time of the cardiac stress test can be subsequently sent to and interpreted by a physician qualified to interpret pulmonary function tests, for an added cost in the range of 5-10% of the cost of the cardiac stress test.

In the absence of this invention, alternatives for the diagnosis and management of exercise-aggravated respiratory disease in patients whose cardiac risks make it unsafe to perform exercise challenges without cardiac monitoring and immediate availability of cardiac resuscitation, are to guess about the role of respiratory disease and treat empirically, to repeat the cardiac stress test in a hospital cardiopulmonary laboratory where a simple pulmonary component can be added, or to perform a complex cardiopulmonary stress test. In the absence of standards for simple cardiopulmonary stress testing in this circumstance most institutional cardiopulmonary laboratories only perform complex cardiopulmonary stress tests, for which there are standard protocols, but with a more invasive procedure that stresses the health care system as well as the patient, with a cost approximately 3 times that of the original cardiac stress test and testing that is overkill for the overwhelming majority of patients who could benefit from the simple tests made possible with enhanced electronic peak flow meters incorporating features of this invention.

There is presently no standard format for reporting simple pulmonary stress test data as an add-on to standard cardiac stress testing. As devices incorporating this feature of the present invention will for the first time create a widespread need for remote reporting of the pulmonary component of such testing by respiratory specialists not associated with the multiple cardiac stress test centers from which tests may need interpretation, it is possible to define a provisional standard data set for this test. See Appendix.

Meters optimized for simple pulmonary stress testing as an add-on to basic cardiac stress testing will have a default program setting for the cardiopulmonary stress test application to display an alert message and give an audible alarm any time a post-exercise FEV1 is down by 20% or more from baseline.

If demand and quantity sales of enhanced electronic peak flow meters for adjunctive simple pulmonary stress testing in cardiopulmonary stress tests are sufficient to result in low unit costs, it is expected to be more cost-effective for high volume cardiac stress test laboratories to purchase multiple units for the simultaneous testing of multiple patients than to ask device designers to create devices able to take data from multiple patients concurrently. These devices would contain effective features to minimize the misrecording of one patient's data as part of a different patient's test, and to minimize the risk of cross-contamination from failure to properly change mouthpieces between patients (which is technically much more difficult). The need for measurements at timed intervals before starting and after completing exercise challenge could complicate testing if it turns out that two patients need the same meter at the same time. Thus it is not anticipated that a significant demand for devices able to record data for multiple concurrent users, However, such devices do constitute a possible additional embodiment of this invention.

Still other practical and useful embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application.

Thus, regardless of the content of any portion (e.g., title, field, background, summary, abstract, drawing figure, etc.) of this application, unless clearly specified to the contrary, such as via an explicit definition, assertion, or argument, with respect to any claim, whether of this application and/or any claim of any application claiming priority hereto, and whether originally presented or otherwise:
- there is no requirement for the inclusion of any particular described or illustrated characteristic, function, activity, or element, any particular sequence of activities, or any particular interrelationship of elements;
- any elements can be integrated, segregated, and/or duplicated;
- any activity can be repeated, any activity can be performed by multiple entities, and/or any activity can be performed in multiple jurisdictions; and
- any activity or element can be specifically excluded, the sequence of activities can vary, and/or the interrelationship of elements can vary.

Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all subranges therein. Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. An electronic peak flow meter comprising:
   a sensor for measuring a respiratory airflow,
   a transducer for converting said respiratory air flow into an electronic value;
   a processor for storing said electronic value in a memory;
   a respiratory data section of said memory for storing a set of said converted electronic values;
   a program stored within said memory for execution by said processor, said program providing a flag for said electronic values identifying an environmental condition in the presence of which said airflows are measured, said processor executing said program to calculate at least one pulmonary function parameter from said set of electronic values and at least one statistical process control variable from a statistical process control mean to determine a pulmonary threshold, said pulmonary threshold being determined by said environmental condition in the presence of which said airflows are measured.

2. The electronic peak flow meter of claim 1 wherein a plurality of said respiratory airflows is taken over a sample period of time.

3. The electronic peak flow meter of claim 1 wherein said pulmonary function parameter is PEER for each respiratory airflow and said statistical process control variable is a standard deviation of said PEFR.

4. The electronic peak flow meter of claim 3 wherein said pulmonary threshold is a plurality of standard deviations of said PEFR for said respiratory airflows and said respiratory airflows are flagged with a common environmental condition.

5. The electronic peak flow meter of claim 1 wherein said pulmonary function parameter is FEV1 for each respiratory airflow and said statistical process control variable is at least one standard deviation of FEV1.

6. The electronic peak flow meter of claim 5 wherein said pulmonary threshold is outside said at least one standard deviation of FEV1 and said respiratory airflows are flagged with a common environmental condition.

7. The electronic peak flow meter of claim 5 wherein said pulmonary threshold is updated by a health care professional based on an analysis of said calculated pulmonary function parameters and said calculated statistical process control variables.

8. The electronic peak flow meter of claim 1 wherein said pulmonary function parameter is PEFR for each respiratory airflow and said statistical process control variable is either an upper process control limit or a lower process limit.

9. A system for evaluating respiratory air flow measurements comprising:
   an electronic peak flow meter having a sensor for measuring a respiratory airflow, a transducer for converting said respiratory air flow into an electronic value and a data port;
   a medical computer having a processor and a memory, said electronic value being stored in said memory, said medical computer also including a respiratory data section for storing a set of said converted electronic values, and a program stored within said memory for execution by said processor, said program providing a flag for said electronic values identifying a environmental condition in the presence of which said airflows are measured; and
   a computer network coupled to said data port and said medical computer wherein said processor executes said program to calculate at least one pulmonary function parameter from said set of electronic values and at least one statistical process control variable from a statistical process control mean to determine a pulmonary threshold, said pulmonary threshold being determined by said environmental condition in the presence of which said airflows were measured.

10. The system for evaluating respiratory air flow measurements of claim 9 wherein a plurality of said respiratory airflows is are taken over a sample period of time.

11. The system for evaluating respiratory air flow measurements of claim 9 wherein said pulmonary function parameter is PEFR for each respiratory airflow and said statistical process control variable is a standard deviation of said PEFR.

12. The system for evaluating respiratory air flow measurements of claim 11 wherein said pulmonary threshold is three standard deviations from said mean PEFR and said respiratory airflows are flagged with a common environmental condition.

13. The system for evaluating respiratory air flow measurements of claim 9 wherein said pulmonary function parameter is FEV1 for each respiratory airflow and said statistical process control variable is a at least one standard deviation of FEV1.

14. The system for evaluating respiratory air flow measurements of claim 13 wherein said pulmonary threshold is at least eight consecutive converted data values outside of said at least one standard deviation of FEV1, all eight data values being on one side of said process control mean, said respiratory airflows being flagged with a common environmental condition.

15. The system for evaluating respiratory air flow measurements of claim 9 wherein said pulmonary threshold is updated by a health care professional based on an analysis of said calculated pulmonary function parameters and said calculated statistical process control variables.

16. A method for determining respiratory function using a computer-based system, comprising said computer-based system performing the steps of:

measuring a respiratory airflow;

converting said respiratory air flow into a set of electronic values;

flagging said electronic values according to an environmental condition in the presence of which said respiratory airflows were taken;

storing said electronic values in a memory;

calculating at least one at least one pulmonary function parameter from said set of said stored electronic values and at least one statistical process control variable from a statistical process control mean; and determining a pulmonary threshold, said pulmonary threshold being determined by said environmental condition in the presence of which said respiratory airflows were taken.

17. The computer-based method of claim 16 wherein said step of measuring is performed repeatedly on a plurality of respiratory airflow samples and said step of storing includes the steps of testing said plurality of respiratory airflow samples and selecting an optimal respiratory airflow sample.

18. The computer-based method of claim 16 wherein said pulmonary function parameter is PEFR and said at least one statistical process control variable is a standard deviation of said PEFR and said pulmonary threshold is a multiple of said standard deviation for said set of respiratory airflows.

19. The computer-based method of claim 16 wherein said step of calculating at least one statistical process control variable includes calculating either an upper process control limit or a lower process limit and said step of determining a pulmonary threshold includes setting said pulmonary threshold at said calculated upper or lower process control limit, said respiratory airflows being flagged with a common environmental condition.

20. The computer-based method of claim 16 further comprising the step of issuing a warning alert when said pulmonary threshold is exceeded.

* * * * *